(12) United States Patent
Hah et al.

(10) Patent No.: US 9,789,086 B1
(45) Date of Patent: Oct. 17, 2017

(54) N-(5-ARYLAMIDO-2-METHYLPHENYL)-5-METHYLISOOXAZOLE-4-CARBOXAMIDE DERAVATIVE, PHARMACEUTICAL ACCEPTABLE SALT THEREOF, METHOD FOR PREPARATION THEROF AND FMS KINASE INHIBITOR COMPRISING THE SAME AS ANACTIVE INGREDIENT

(71) Applicant: Industry-University Cooperation Foundation Hanyang University ERICA Campus, Ansan (KR)

(72) Inventors: Jung-Mi Hah, Seoul (KR); Kyung Jin Jung, Seoul (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 15/510,755

(22) PCT Filed: Sep. 17, 2015

(86) PCT No.: PCT/KR2015/009787
§ 371 (c)(1),
(2) Date: Mar. 13, 2017

(87) PCT Pub. No.: WO2016/047967
PCT Pub. Date: Mar. 31, 2016

(30) Foreign Application Priority Data

Sep. 22, 2014 (KR) .................. 10-2014-0125813

(51) Int. Cl.
*A61K 31/415* (2006.01)
*C07D 261/06* (2006.01)
*C07C 233/07* (2006.01)
*C07C 233/10* (2006.01)

(52) U.S. Cl.
CPC .......... *A61K 31/415* (2013.01); *C07C 233/07* (2013.01); *C07C 233/10* (2013.01); *C07D 261/06* (2013.01)

(58) Field of Classification Search
None
See application file for complete search history.

(56) References Cited

U.S. PATENT DOCUMENTS

| 6,316,479 B1 | 11/2001 | McMahon |
| 6,458,960 B1 | 10/2002 | Morohashi |

FOREIGN PATENT DOCUMENTS

| KR | 10-2014-0002476 | 1/2014 |
| KR | 10-2014-0086002 | 7/2014 |
| WO | 03-013517 | 2/2003 |
| WO | 2008-052974 | 5/2008 |

OTHER PUBLICATIONS

KIPO, PCT Search Report & Written Opinion of Application PCT/KR2015/009787, dated Jun. 20, 2016.
Mangold, U. et al., "Identification and characterization of potential new therapeutic targets in inflammatory and autoimmune diseases", Eur. J. Biochem., Dec. 15, 1999, pp. 1184-1191.
Im, D. et al., "Discovery of 4-arylamido 3-methyl isoxazole derivatives as novel FMS kinase inhibitors", Eur. J. Med. Chem., Aug. 18, 2015, pp. 600-610.
Mohammed I. El-Gamal et al., "FMS Kinase Inhibitors: Current Status and Future Prospects", Medicinal Research Reviews, 33, No. 3, 599-636, Published online Mar. 20, 2012 in Wiley Online Library (wileyonlinelibrary.com).
Blume-Jensen P, Hunter T., "Oncogenic kinase signaling", Nature, vol. 411, May 17, 2001, pp. 355-365.

*Primary Examiner* — Kamal Saeed
(74) *Attorney, Agent, or Firm* — Lex IP Meister, PLLC

(57) ABSTRACT

The present invention relates to N-(5-arylamido-2-methylphenyl)-5-methylisoquoxazole-4-carboxamide derivative, or a pharmaceutically acceptable salt thereof and a pharmaceutical composition comprising same. The compound according to the present invention exhibits an FMS kinase inhibitory activity and thus can be used as pharmaceutical composition for preventing and treating diseases associated therewith.

10 Claims, No Drawings

N-(5-ARYLAMIDO-2-METHYLPHENYL)-5-METHYLISOOXAZOLE-4-CARBOXAMIDE DERAVATIVE, PHARMACEUTICAL ACCEPTABLE SALT THEREOF, METHOD FOR PREPARATION THEROF AND FMS KINASE INHIBITOR COMPRISING THE SAME AS ANACTIVE INGREDIENT

TECHNICAL FIELD

The present invention relates to a novel compound that can be effectively used as an FMS kinase inhibitor.

BACKGROUND OF ART

Receptor tyrosine kinases (RTKs) are cell surface receptors of numerous important growth factors and hormones that involves in the intracellular signal transduction process. In addition to these intracellular regulatory roles, RTKs are also deeply involved in the onset and progression of many cancers. In such cancers, gene translocation occurs, resulting in a kinase fusion protein with non-specific activity.

Identification of translocation and mutation of cancers is crucial to the development of a selective new treatment method of fusion or mutant proteins and allows the development of anticancer drugs with low side effects and selective activity. For example, imatinib mesylate (Gleeve) is the first kinase inhibitor used as an anticancer agent and is effective in the treatment of CML (Chronic Myelogenous Leukemia) caused by the inhibition of BCR-ABL kinase.

As human RTKs, 58 types of RTKs belonging to 20 families have been identified (Blume-Jensen P, Hunter T. Oncogenic kinase signaling. Nature 2001; 411: 355-365). Among them, FMS kinase (c-fms; cellular Feline McDonough Sarcoma) is also called CSF-1R (colony-stimulating factor-1 receptor) and is a member of the gene group first isolated from the feline sarcoma virus Susan McDonough strains.

FMS kinase is a receptor for macrophage-colony-stimulating factor (M-CSF) and is classified as type III receptor tyrosine kinase (class III RTK) with Kit, Flt-3, and PDGFR. It is encoded by a primary oncogenic gene (c-fms proto-oncogene). M-CSF is also called CSF-1, and M-CSF is an important growth factor that involves in immune and inflammatory responses, bone metabolism and pregnancy. In addition, as FMS kinase participates in the process that monocytes activate into macrophages and differentiates into osteoclasts, it plays an important role in inflammation and bone erosion.

Therefore, overexpression of M-CSF or overexpression of its receptor, FMS, is closely associated with the growth and metastasis of cancer, and also is deeply associated with osteoporosis, rheumatoid arthritis, inflammatory diseases such as rheumatoid arthritis, Crohn's disease, etc. (El-Gamal M I et al., FMSKinase Inhibitors: Current Status and Future Prospects. Med Res Rev. 2013 May; 33 (3): 599-636).

Thus, there is a demand to develop a compound capable of inhibiting the activity of FMS kinase, and for example, such compound is disclosed in Korean Patent Publication No. 10-2014-0086002, Korean Patent Publication No. 10-2014-0002476, etc.

Therefore, the present inventors have studied the structure of a novel compound capable of inhibiting the activity of FMS kinase and found that N-(5-arylamido-2-methylphenyl)-5-methylisoquoxazole-4-carboxamide derivative has FMS kinase inhibitory activity, thereby completing the present invention.

DETAILED DESCRIPTION OF THE INVENTION

Technical Problem

The present invention provides a compound represented by Chemical Formula 1 below, or a pharmaceutically acceptable salt thereof.

Further, the present invention also provides a method for preparing a compound represented by Chemical Formula 1 below.

In addition, the present invention provides a pharmaceutical composition for the prevention or treatment of FMS kinase-associated diseases comprising a compound represented by Chemical Formula 1 below or a pharmaceutically acceptable salt thereof as an active ingredient, and a method for preparing thereof.

Technical Solution

In order to achieve the above objects, the present invention provides a compound represented by the following Chemical Formula 1, or a pharmaceutically acceptable salt thereof:

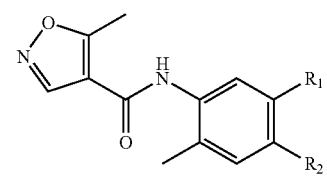

[Chemical Formula 1]

wherein:

$R_1$ is hydrogen and $R_2$ is $R_3$, or $R_1$ is $R_3$ and $R_2$ is hydrogen, $R_3$ is —NHCO—$R_4$, —NHCONH—$R_5$, or —NHSO$_2$—$R_6$, $R_4$ is (1H-indol-3-yl)methyl; 1-acetylpiperidin-4-yl; 1-phenyl-5-(trifluoromethyl)-1H-pyrazolyl; 6-hydroxy-2,5,7,8-tetramethylchroman-2-yl; benzotriazolyl; biphenyl; di(4-chlorophenyl)methyl; indolinyl; pyrazinyl; pyridinyl; quinolinyl; phenyl substituted with one or two substituents each independently selected from the group consisting of $C_{1-4}$ alkyl, $C_{1-4}$ haloalkyl, halogen, morpholino, imidazolyl substituted with methyl, piperazinyl substituted with methyl, and cyanophenylthio; or benzyl substituted with halogen or phenyl, $R_5$ is phenyl substituted with one or two substituents each independently selected from the group consisting of $C_{1-4}$ haloalkyl and halogen, and $R_6$ is $C_{1-4}$ alkyl.

In Chemical Formula 1, only one substituent of $R_1$ and $R_2$ is $R_3$, and $R_3$ can have three types of substituents.

When $R_3$ is —NHCONH—$R_5$, preferably $R_4$ is (1H-indol-3-yl)methyl; 1-acetylpiperidin-4-yl; 1-phenyl-5-(trifluoromethyl)-1H-pyrazolyl; 6-hydroxy-2,5,7,8-tetramethylchroman-2-yl; 1H-benzo[d][1,2,3]triazol-5-yl; biphenyl-2-yl; biphenyl-4-yl; di(4-chlorophenyl)methyl; indolin-2-yl; pyrazin-2-yl; pyridin-4-yl; quinolin-2-yl; quinolin-3-yl; phenyl substituted by one or two substituents each independently selected from the group consisting of methyl, trifluoromethyl, chloro, morpholino, 2-methyl-1H-imidazol-1-yl, 4-methyl-1H-imidazol-1-yl, 5-methyl-1H-imidazole-1-yl, 4-methylpiperazin-1-yl and cyanophenylthio; or benzyl substituted with fluoro or phenyl.

Also, when $R_3$ is —NHCONH—$R_5$, preferably $R_5$ is phenyl substituted with one or two substituents each independently selected from the group consisting of trifluoromethyl, fluoro, and chloro.

Further, when $R_3$ is —NHSO$_2$—$R_6$, preferably $R_6$ is propyl.

Also preferably $R_1$ is $R_3$ and $R_2$ is hydrogen, $R_3$ is —NHCO—$R_4$, $R_4$ is 1-phenyl-5-(trifluoromethyl)-1H-pyrazolyl; or phenyl substituted with two substituents each independently selected from the group consisting of $C_{1-4}$ haloalkyl, morpholino, imidazolyl substituted with methyl, and piperazinyl substituted with methyl. More preferably, $R_4$ is phenyl substituted with two substituents, wherein one substituent is $C_{1-4}$ haloalkyl, and the other substituent is selected from the group consisting of morpholino, imidazolyl substituted with methyl, and piperazinyl substituted with methyl. More preferably, $R_4$ is phenyl substituted with two substituents, wherein one substituent is trifluoroalkyl and the other substituent is selected from the group consisting of morpholino, 2-methyl-1H-imidazol-1-yl, 4-methyl-1H-imidazol-1-yl, 5-methyl-1H-imidazol-1-yl and 4-methylpiperazine-1-yl.

Typical examples of the compounds represented by Chemical Formula 1 are as follows:

1) 5-methyl-N-(2-methyl-4-(4-morpholino-3-(trifluoromethyl)benzamido)phenyl)isoxazole-4-carboxamide,
2) 5-methyl-N-(2-methyl-4-(3-(4-methylpiperazin-1-yl)-5-(trifluoromethyl)benzamido)phenyl)isoxazole-4-carboxamide,
3) 5-methyl-N-(2-methyl-5-(3-(4-methylpiperazin-1-yl)-5-(trifluoromethyl)benzamido)phenyl)isoxazole-4-carboxamide,
4) 5-methyl-N-(2-methyl-5-(4-morpholino-3-(trifluoromethyl)benzamido)phenyl)isoxazole-4-carboxamide,
5) N-(5-(4-chloro-3-(trifluoromethyl)benzamido)-2-methylphenyl)-5-methylisoxazole-4-carboxamide,
6) N-(5-(3-chlorobenzamido)-2-methylphenyl)-5-methylisoxazole-4-carboxamide,
7) N-(5-(4-chlorobenzamido)-2-methylphenyl)-5-methylisoxazole-4-carboxamide,
8) N-(5-(2-(2-fluorophenyl)acetamido)-2-methylphenyl)-5-methylisoxazole-4-carboxamide,
9) 5-methyl-N-(2-methyl-5-(3-(2-methyl-1H-imidazol-1-yl)-5-(trifluoromethyl)benzamido)phenyl)isoxazole-4-carboxamide,
10) 5-methyl-N-(2-methyl-5-(3-(5-methyl-1H-imidazol-1-yl)-5-(trifluoromethyl)benzamido)phenyl)isoxazole-4-carboxamide,
11) 5-methyl-N-(2-methyl-5-(3-(4-methyl-1H-imidazol-1-yl)-5-(trifluoromethyl)benzamido)phenyl)isoxazole-4-carboxamide,
12) 5-methyl-N-(2-methyl-5-(quinoline-2-carboxamido)phenyl)isoxazole-4-carboxamide,
13) N-(5-(2,2-bis(4-chlorophenyl)acetamido)-2-methylphenyl)-5-methylisoxazole-4-carboxamide,
14) N-(5-(6-hydroxy-2,5,7,8-tetramethylchroman-2-carboxamido)-2-methylphenyl)-5-methylisoxazole-4-carboxamide,
15) N-(5-(1-acetylpiperidine-4-carboxamido)-2-methylphenyl)-5-methylisoxazole-4-carboxamide,
16) N-(5-(2-(1H-indol-3-yl)acetamido)-2-methylphenyl)-5-methylisoxazole-4-carboxamide,
17) 5-methyl-N-(2-methyl-5-(pyrazine-2-carboxamido)phenyl)isoxazole-4-carboxamide,
18) N-(5-(1H-benzo[d][1,2,3]triazole-5-carboxamido)-2-methylphenyl)-5-methylisoxazole-4-carboxamide,
19) N-(5-(indoline-2-carboxamido)-2-methylphenyl)-5-methylisoxazole-4-carboxamide,
20) N-(5-(isonicotinamido)-2-methylphenyl)-5-methylisoxazole-4-carboxamide,
21) N-(5-(2-(2-cyanophenylthio)benzamido)-2-methylphenyl)-5-methylisoxazole-4-carboxamide,
22) N-(5-(2-(biphenyl-4-yl)acetamido)-2-methylphenyl)-5-methylisoxazole-4-carboxamide,
23) 5-methyl-N-(2-methyl-5-(1-phenyl-5-(trifluoromethyl)-1H-pyrazole-4-carboxamido)phenyl)isoxazole-4-carboxamide,
24) N-(5-(3,5-dimethylbenzamido)-2-methylphenyl)-5-methylisoxazole-4-carboxamide,
25) N-(5-biphenyl-2-ylcarboxamido-2-methylphenyl)-5-methylisoxazole-4-carboxamide,
26) N-(5-biphenyl-4-ylcarboxamido-2-methylphenyl)-5-methylisoxazole-4-carboxamide,
27) 5-methyl-N-(2-methyl-5-(quinoline-3-carboxamido)phenyl)isoxazole-4-carboxamide,
28) N-(5-(3-(4-chlorophenyl)ureido)-2-methylphenyl)-5-methylisoxazole-4-carboxamide,
29) 5-methyl-N-(2-methyl-5-(3-(3-(trifluoromethyl)phenyl)ureido)phenyl)isoxazole-4-carboxamide,
30) N-(5-(3-(4-chloro-3-(trifluoromethyl)phenyl)ureido)-2-methylphenyl)-5-methylisoxazole-4-carboxamide,
31) N-(5-(3-(2-fluorophenyl)ureido)-2-methylphenyl)-5-methylisoxazole-4-carboxamide,
32) N-(5-(3-(3-chlorophenyl)ureido)-2-methylphenyl)-5-methylisoxazole-4-carboxamide,
33) N-(5-(3-(3,5-dichlorophenyl)ureido)-2-methylphenyl)-5-methylisoxazole-4-carboxamide,
34) N-(5-(3-(3,4-dichlorophenyl)ureido)-2-methylphenyl)-5-methylisoxazole-4-carboxamide,
35) N-(4-(3-(4-chloro-3-(trifluoromethyl)phenyl)ureido)-2-methylphenyl)-5-methylisoxazole-4-carboxamide,
36) 5-methyl-N-(2-methyl-4-(3-(3-(trifluoromethyl)phenyl)ureido)phenyl)isoxazole-4-carboxamide,
37) N-(4-(3-(3-chlorophenyl)ureido)-2-methylphenyl)-5-methylisoxazole-4-carboxamide,
38) N-(4-(3-(2-fluorophenyl)ureido)-2-methylphenyl)-5-methylisoxazole-4-carboxamide,
39) N-(4-(3-(4-chlorophenyl)ureido)-2-methylphenyl)-5-methylisoxazole-4-carboxamide,
40) N-(4-(3-(3,4-dichlorophenyl)ureido)-2-methylphenyl)-5-methylisoxazole-4-carboxamide,
41) N-(4-(3-(3,5-dichlorophenyl)ureido)-2-methylphenyl)-5-methylisoxazole-4-carboxamide,
42) 5-methyl-N-(2-methyl-5-(propylsulfonamido)phenyl)isoxazole-4-carboxamide,
43) 5-methyl-N-(2-methyl-4-(propylsulfonamido)phenyl)isoxazole-4-carboxamide, and
44) 5-methyl-N-(2-methyl-5-(3-morpholino-5-(trifluoromethyl)benzamido)phenyl)isoxazole-4-carboxamide.

Further, the compounds represented by Chemical Formula 1 may form a pharmaceutically acceptable salt. Suitable pharmaceutically acceptable salts are those conventionally used in the art, such as acid addition salts, and are not particularly limited. Preferred pharmaceutically acceptable acid addition salts include, for example, inorganic acids such as hydrochloric acid, hydrobromic acid, phosphoric acid, orthophosphoric acid or sulfuric acid; or organic acids such as, for example, methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid or acetylsalicylic acid.

In addition, the compound represented by Chemical Formula 1 includes all possible solvates and hydrates, and also includes all possible isomers. Solvates, hydrates and isomers of the compounds of Chemical Formula 1 may be prepared using conventional methods.

Moreover, the compound represented by Chemical Formula 1 may be prepared in a crystalline form or an amorphous form, and when the compound of Chemical Formula 1 is prepared in crystalline form, it can be optionally hydrated or solvated.

Further, the present invention provides a method for preparing the compound represented by Chemical Formula 1, as shown in the following Reaction Formula 1.

Step 1 is a step of preparing a compound represented by Chemical Formula 3 by reacting a compound represented by Chemical Formula 2 with $SOCl_2$, wherein —OH in the carboxy group is substituted with —Cl.

Step 2 is a step of preparing a compound represented by Chemical Formula 4 by reacting a compound represented by Chemical Formula 3 with 2-methyl-4-nitroaniline or 2-methyl-5-nitroaniline. As a solvent, THF may be used.

Step 3 is a step of preparing a compound represented by Chemical Formula 5 by reacting a compound represented by Chemical Formula 4 with $SnCl_2$, wherein the nitro group is substituted with an amine group. As a solvent, ethanol may be used.

Step 4-1 to Step 4-3 are classified according to the type of $R_3$ in Chemical Formula 1. First, Step 4-1 is a step of preparing a compound in which $R_3$ is —NHCO—$R_4$ by reacting a compound represented by Chemical Formula 5 with $R_4$—COOH or $R_4$—COCl. It is preferable to use HATU together, and DMF or THF can be used as a solvent Step 4-2 is a step of preparing a compound in which $R_3$ is —NHCONH—$R_5$ by reacting a compound represented by

[Reaction Scheme 1]

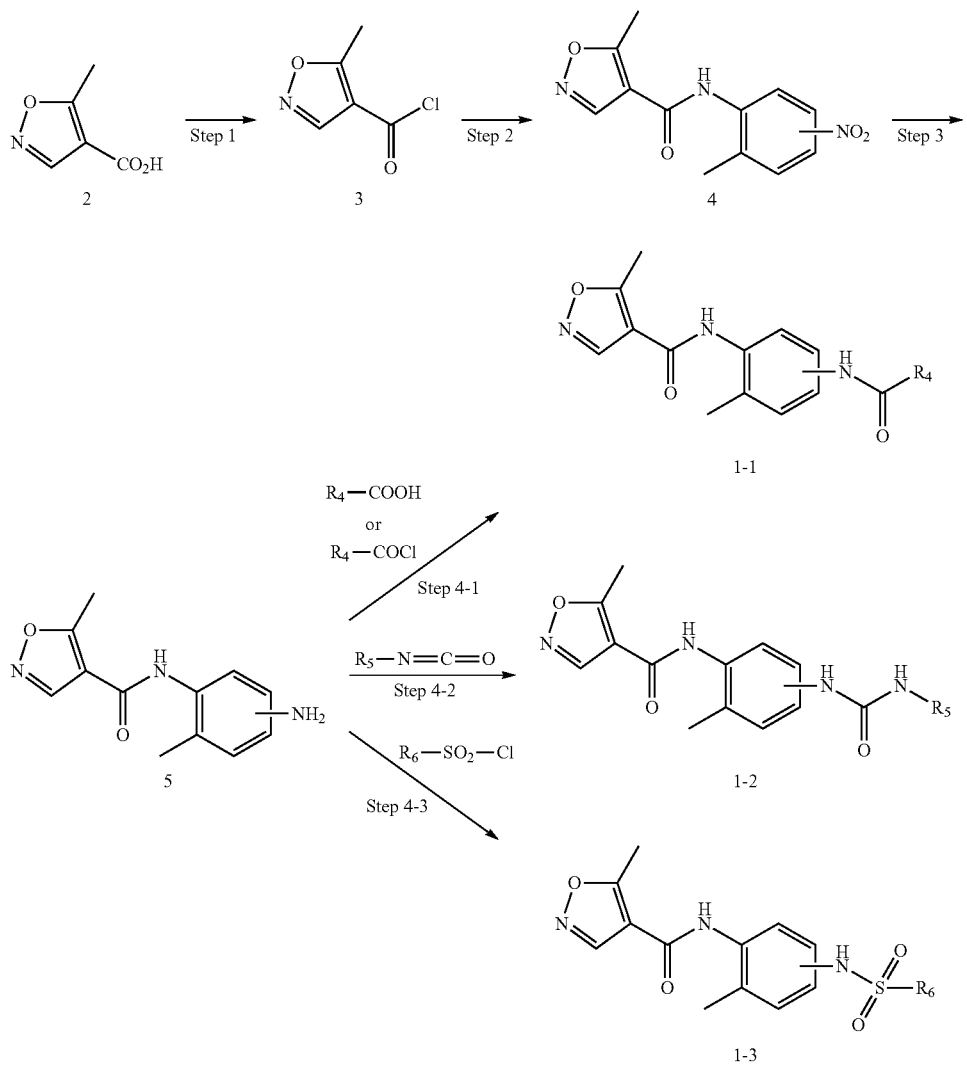

(in Reaction Scheme 1, $R_4$, $R_5$ and $R_6$ are as previously defined)

Chemical Formula 5 with $R_5$—N=C=O. As a solvent, THF may be used. Step 4-3 is a step of preparing a compound in which $R_3$ is —NHSO$_2$—$R_6$ by reacting a compound represented by Chemical Formula 5 with $R_6$—SO$_2$—Cl. As a solvent, methylene chloride can be used.

In addition, the present invention provides a pharmaceutical composition for the prevention or treatment of FMS kinase-associated diseases comprising a compound represented by Chemical Formula 1 or a pharmaceutically acceptable salt thereof as an active ingredient. Further, the present invention provides a method for preventing or treating FMS kinase-associated diseases comprising administering a compound represented by Chemical Formula 1 or a pharmaceutically acceptable salt thereof to a subject in need of the prevention or treatment of FMS kinase-associated diseases.

Examples of FMS kinase-associated diseases may include a cancer or an inflammatory disease. More specifically, the FMS kinase-associated diseases include leukemia, osteoporosis, rheumatoid arthritis or Crohn's disease.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient. In the case in which the pharmaceutical composition is formulated, generally used diluents or excipients such as fillers, extenders, binders, wetting agents, disintegrants, surfactants, or the like, may be used.

Solid preparations for oral administration include tablets, pills, powders, granules, capsules, troches, and the like, and these solid preparations may be prepared by mixing the compound of Chemical Formula 1 according to the present invention, its isomer or its pharmaceutically acceptable salt, hydrate or solvate with at least one excipient, for example, starch, calcium carbonate, sucrose, lactose, gelatin, or the like.

Liquid preparations for oral administration include suspensions, liquids for internal use, emulsions, syrups, and the like, and various excipients such as a wetting agent, a sweetener, a flavoring agent, a preserving agent, or the like, as well as water and liquid paraffin that are generally used diluents may be contained.

Formulations for parenteral administration include sterile aqueous solutions, non-aqueous solvents, suspensions, emulsions, freeze-dried formulations, and suppositories. As the non-aqueous solvent or the suspensions, propylene glycol, polyethylene glycol, vegetable oil such as olive oil, injectable esters such as ethyloleate, or the like, may be used.

A preferred dose of the compound of Chemical Formula 1 according to the present invention or a pharmaceutically acceptable salt thereof may be varied according to the condition and weight of a patient, the severity of a disease, the type of a drug, and the route and duration of administration, but it may be suitably selected according to a method generally applied in the technical field to which it belongs. Further, the pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

In addition, the compound of Chemical Formula 1 according to the present invention or a pharmaceutically acceptable salt thereof itself has activity, but after it was absorbed into the body, a special environment inside the body or products of metabolic pathways, the possibility of exhibiting a pharmacological action as an efficacy agent is not excluded.

Advantageous Effects

The compound represented by Chemical Formula 1 according to the present invention or a pharmaceutically acceptable salt thereof exhibits FMS kinase inhibitory activity and thus can be used as a pharmaceutical composition for the prevention or treatment of a disease associated therewith.

DETAILED DESCRIPTION OF THE EMBODIMENTS

Below, the present invention will be described in more detail by way of examples. However, these examples are provided only for illustration of the present invention, and should not be construed as limiting the scope of the present invention to these examples.

Preparation Example 1: Preparation of N-(4-amino-2-methylphenyl)-5-methylisoxazole-4-carboxamide

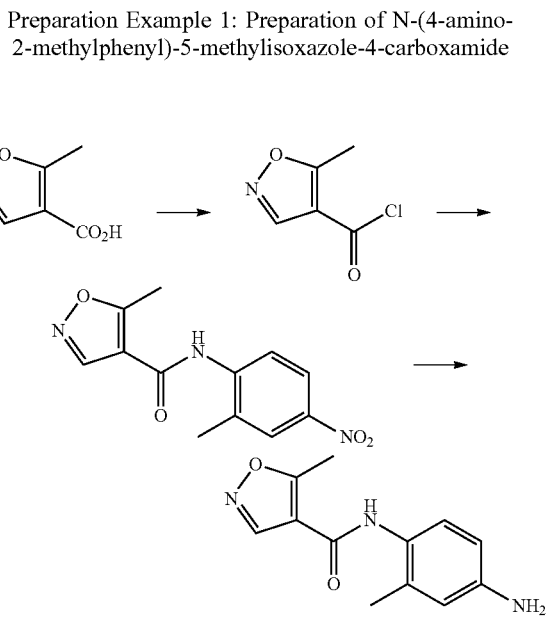

Step 1: Preparation of 5-methylisoxazole-4-carbonyl chloride 5-methylisoxazole-4-carboxylic acid (1 g, 7.86 mmol) was added to SOCl$_2$ (3 mL) and stirred at 50° C. After completion of the reaction, the reaction mixture was cooled, and then the volatile materials were removed by distillation under reduced pressure to give the title compound (crude yellow oil, 96%).

$^1$H NMR (400 MHz, DMSO) δ 8.77 (1H, s), 2.64 (3H, s)

Step 2: Preparation of 5-methyl-N-(2-methyl-4-nitrophenyl)isoxazole-4-carboxamide 5-methylisoquioxazole-4-carbonyl chloride (1.1 g, 7.55 mmol) prepared in Step 1 and 2-methyl-4-nitroaniline (1.15 g, 7.55 mmol) were added to THF (75 mL), and the mixture was stirred at 65° C. until 5-methylisoooxazole-4-carbonyl chloride was disappeared. After cooling, the solvent was removed by distillation under reduced pressure, and the residue was purified by column chromatography (EA:Hex=1:3) to give the title compound (yellow solid, 65%).

$^1$H NMR (400 MHz, DMSO) δ 9.91 (1H, s), 9.06 (1H, s), 8.19 (1H, s), 8.11 (1H, t, J=2.8 Hz), 7.79 (1H, t, J=4.4 Hz), 2.68 (3H, s), 2.38 (3H, s)

Step 3: Preparation of N-(4-amino-2-methylphenyl)-5-methylisoxazole-4-carboxamide 5-methyl-N-(2-methyl-4-nitrophenyl)isoxazole-4-carboxamide (460 mg, 1.76 mmol) prepared in Step 2, 35% HCl (0.69 mL) and SnCl$_2$2H$_2$O (1.98 g, 8.80 mmol) was added to EtOH (3.5 mL) and stirred at 80° C. After completion of the reaction, the reaction mixture was cooled to room temperature and distilled under reduced pressure to remove the solvent. The pH was adjusted to 7 to 8 with a aqueous sodium hydrogen carbonate solution and extracted with ethyl acetate. The organic layer was dried over anhydrous sodium sulfate, distilled under reduced pressure and purified by column chromatography (silica gel, MC:MeOH=10:1) to give the title compound (yellow solid, 61%).

$^1$H NMR (400 MHz, DMSO) δ 9.42 (1H, s), 9.01 (1H, s), 6.87 (1H, d, J=8.4 Hz), 6.44 (1H, s), 6.40 (1H, dd, J=2.4 Hz, J=2.4 Hz), 5.06 (2H, —NH, br, s), 2.64 (3H, s), 2.04 (3H, s)

Preparation Example 2: Preparation of N-(5-amino-2-methylphenyl)-5-methylisoxazole-4-carboxamide

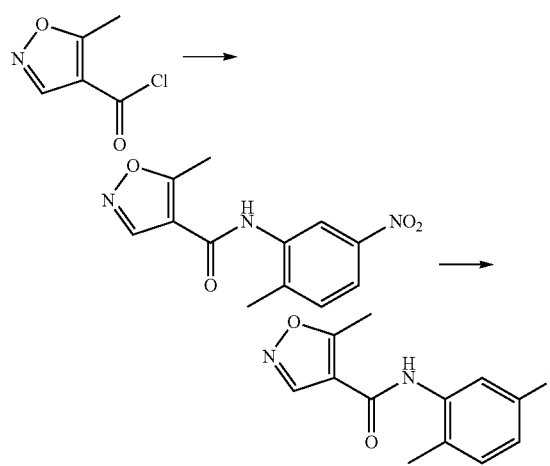

Step 1: Preparation of 5-methy-N-(2-methyl-4-nitrophenyl)isoxazole-4-carboxamide 5-methylisoxazole-4-carbonyl chloride (500 mg, 3.43 mmol) prepared in Step 1 of Preparation Example 1 and 2-methyl-5-nitroaniline (521.8 mg, 3.43 mmol) were added to THF (34 ml), and the mixture was stirred at 65° C. until 5-methylisoooxazole-4-carbonyl chloride was disappeared. After cooling, the solvent was removed by distillation under reduced pressure and the residue was purified by column chromatography (EA/Hex=1:3) to give the title compound (yellow solid, 52%).

$^1$H NMR (400 MHz, DMSO) δ 9.94 (1H, s), 9.05 (1H, s), 8.33 (1H, s), 8.04 (1H, t, J=4.0 Hz), 7.58 (1H, d, J=8), 2.68 (3H, s), 2.37 (3H, s)

Step 2: Preparation of N-(5-amino-2-methylphenyl)-5-methylisoxazole-4-carboxamide 5-methyl-N-(2-methyl-4-nitrophenyl)isoxazole-4-carboxamide (470 mg, 1.79 mmol) prepared in Step 1, 35% HCl (0.70 mL) and SnCl$_2$2H$_2$O (2.01 g, 8.95 mmol) were added to EtOH (3.5 mL) and stirred at 80° C. After completion of the reaction, the reaction mixture was cooled to room temperature, and the solvent was removed by distillation under reduced pressure. The pH was adjusted to 7 to 8 with a aqueous sodium hydrogen carbonate solution and extracted with ethyl acetate. The organic layer was dried over anhydrous sodium sulfate, distilled under reduced pressure and purified by column chromatography (silica gel, MC:MeOH=10:1) to give the title compound (yellow solid, 60%).

$^1$H NMR (400 MHz, DMSO) δ 9.47 (1H, s), 9.00 (1H, s), 6.89 (1H, d, J=8.4 Hz), 6.56 (1H, d, J=2.0 Hz), 6.40 (1H, dd, J=2.4 Hz, J=2.4 Hz), 4.94 (2H, —NH, br, s), 2.65 (3H, s), 2.03 (3H, s)

Example 1) Preparation of 5-methyl-N-(2-methyl-4-(4-morpholino-3-(trifluoromethyl)benzamido)phenyl)isoxazole-4-carboxamide

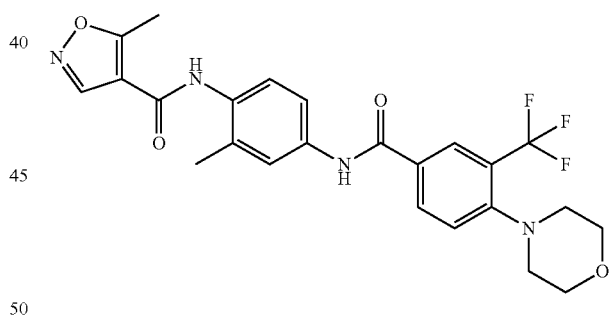

N-(4-amino-2-methylphenyl)-5-methylisoxazole-carboxamide (20 mg, 0.09 mmol) prepared in Preparation Example 1, 3-morpholino-4-(trifluoromethyl)benzoic acid (24.22 mg, 0.09 mmol) and HATU (49.4 mg, 0.13 mmol) were added to DMF (0.88 mL) and stirred at 45° C. The mixture was extracted with ethyl acetate and then washed with saturated sodium hydrogen carbonate aqueous solution. The organic layer was dried over Na$_2$SO$_4$ and purified by column chromatography (silica gel, MC:MeOH=20:1) to give the title compound (white solid, 11%).

$^1$H NMR (400 MHz, DMSO) δ 10.33 (1H, s), 9.76 (1H, s), 8.24-8.21 (2H, m), 7.81 (1H, d, J=2.0 Hz), 7.65 (1H, d, J=8.0 Hz), 7.58 (1H, s), 7.25 (1H, d, J=8.4 Hz), 3.73-3.71 (4H, m), 2.95-2.93 (4H, m), 2.68 (3H, s), 2.15 (3H, s); HRMS (ESI) calculated for Ca$_{24}$H$_{23}$F$_3$N$_4$O$_4$ [M+H]$^+$: 489.1671, found 489.3348. 489.1672.

Example 2) Preparation of 5-methy-N-(2-methyl-4-(3-(4-methylpiperazin-1-yl)-5-(trifluoromethyl)benzamido)phenyl)isoxazole-4-carboxamide

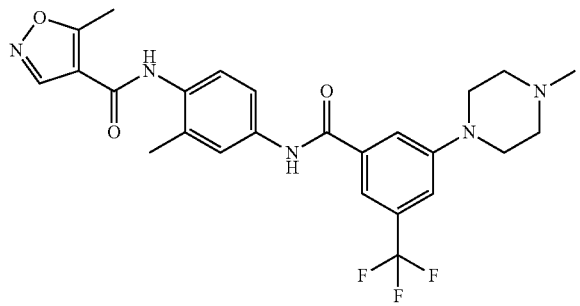 [SMILES: Cc1cc(NC(=O)c2cc(N3CCN(C)CC3)cc(C(F)(F)F)c2)ccc1NC(=O)c1cnoc1C]

The title compound (white solid, 9%) was prepared in the same manner as in Example 1, except that 3-(4-methylpiperazin-1-yl)-5-((trifluoromethyl)benzoic acid was used instead of 3-morpholino-4-(trifluoromethyl)benzoic acid.

$^{1}$H NMR (400 MHz, DMSO) δ 10.35 (1H, s), 9.78 (1H, s), 9.03 (1H, s), 7.81 (1H, d, J=2.0 Hz), 7.71 (1H, s), 7.61-7.57 (2H, m), 7.37 (1H, s), 7.27 (1H, d, J=8.4 Hz), 2.67 (3H, s), 2.24-2.21 (6H, m); HRMS (ESI) calculated for $C_{25}H_{26}F_3N_5O_3$ [M+H]$^+$: 502.1988, found 502.3596. 502.1993.

Example 3) Preparation of 5-methyl-N-(2-methy-5-(3-(4-methylpiperazin-1-yl)-5-(trifluoromethyl)benzamido)phenyl)oxazole-4-carboxamide

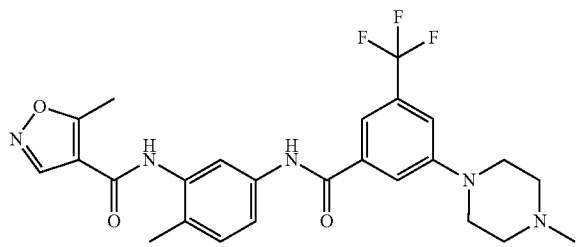 [SMILES: Cc1ccc(NC(=O)c2cc(N3CCN(C)CC3)cc(C(F)(F)F)c2)cc1NC(=O)c1cnoc1C]

N-(5-amino-2-methylphenyl)-5-methylisoxazole-4-carboxamide (25 mg, 0.11 mmol)) prepared in Preparation Example 2, 3-(4-methyl-piperazin-1-yl)-5-trifluoromethyl-benzoic acid (31.13 mg, 0.11 mmol) and HATU (61.75 mg, 0.16 mmol) were added to DMF (1.1 mL) and stirred at 45° C. The mixture was extracted with ethyl acetate, and then washed with a saturated aqueous sodium hydrogen carbonate solution. The organic layer was dried over $Na_2SO_4$ and purified by column chromatography (silica gel, MC:MeOH=20:1) to give the title compound (white solid, 16%).

$^{1}$H NMR (400 MHz, DMSO) δ 10.36 (1H, s), 9.78 (1H, s), 9.06 (1H, s), 7.81 (1H, d, J=2.0 Hz), 7.71 (1H, s), 7.61-7.57 (2H, m), 7.37 (1H, s), 7.27 (1H, d, J=8.4 Hz), 2.68 (3H, s), 2.24-2.21 (6H, m); HRMS (ESI) calculated for $C_{25}H_{26}F_3N_5O_3$ [M+H]$^+$: 502.1988, found 502.2390. 502.1995.

The following Examples 4 to 8 were prepared in the same manner as in Example 3, except that the compounds corresponding to the structures of the compounds to be prepared were used instead of 3-(4-methyl-piperazin-1-yl)-5-trifluoromethyl-benzoic acid.

Example 4) Preparation of 5-methy-N-(2-methyl-5-(4-morpholino-3-(trifluoromethyl)benzamido)phenyl)isoxazole-4-carboxamide

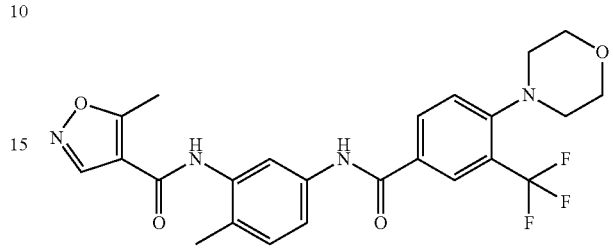

white solid, yield: 9%

$^{1}$H NMR (400 MHz, DMSO) δ 10.37 (1H, s), 9.76 (1H, s), 8.24-8.21 (2H, m), 7.81 (1H, d, J=2.0 Hz), 7.65 (1H, d, J=8.0 Hz), 7.58-7.55 (1H, m), 7.25 (1H, d, J=8.4 Hz), 3.73-3.71 (4H, m), 2.95-2.93 (4H, m), 2.67 (3H, s), 2.19 (3H, s); HRMS (ESI) calculated for $C_{24}H_{23}F_3N_4O_4$ [M+H]$^+$: 489.1671, found 489.2651. 489.1680.

Example 5) Preparation of N-(5-(4-chloro-3-(trifluoromethyl)benzamido)-2-methylphenyl)-5-methyl-isoxazole-4-carboxamide

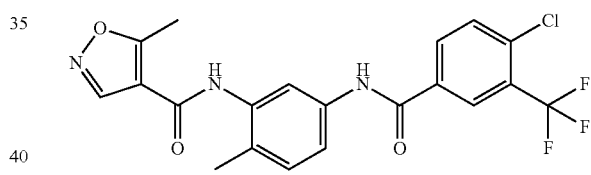

white solid, yield: 9%

$^{1}$H NMR (400 MHz, DMSO) δ 10.53 (1H, s), 9.77 (1H, s), 9.05 (1H, s), 8.39 (1H, s), 8.38-8.24 (1H, m), 7.93 (1H, d, J=8.4 Hz), 7.83 (1H, d, J=2 Hz), 7.59 (1H, dd, J=2.4 Hz), 7.28 (1H, d, J=8.4 Hz), 2.68 (3H, s), 2.21 (3H, s); HRMS (ESI) calculated for $C_{20}H_{15}ClF_3N_3O_3$ [M+H]$^+$: 438.0754, found 438.2612. 438.0759.

Example 6) Preparation of N-(5-(3-chlorobenzamido)-2-methylphenyl)-5-methylisoxazole-4-carboxamide

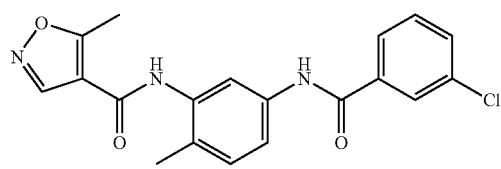 [SMILES: Cc1ccc(NC(=O)c2cccc(Cl)c2)cc1NC(=O)c1cnoc1C]

white solid, yield: 11%

$^{1}$H NMR (400 MHz, DMSO) δ 10.36 (1H, s), 9.77 (1H, s), 9.06 (1H, s), 8.01 (1H, d, J=1.6 Hz), 7.92 (1H, d, J=7.6 Hz), 7.84 (1H, s), 7.67-7.65 (1H, m), 7.59-7.55 (2H, m), 7.26 (1H, d, J=8.4 Hz), 2.68 (3H, s), 2.20 (3H, s); HRMS (ESI) calculated for $C_{19}H_{16}ClN_3O_3$ [M+H]$^+$: 370.0880, found 370.0493. 370.0887.

Example 7) Preparation of N-(5-(4-chlorobenzamido)-2-methylphenyl)-5-methylisoxazole-4-carboxamide

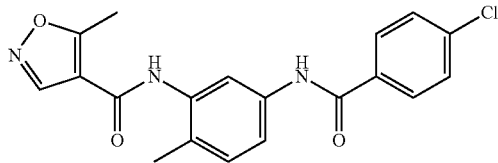 [SMILES: Cc1ccc(NC(=O)c2ccc(Cl)cc2)cc1NC(=O)c1cnoc1C]

white solid, yield: 11%

$^1$H NMR (400 MHz, DMSO) δ 10.34 (1H, s), 9.78 (1H, s), 9.06 (1H, s), 7.99-7.97 (2H, m), 7.83 (1H, s), 7.61-7.55 (3H, m), 7.24 (1H, d, J=4.8 Hz), 2.67 (3H, s), 2.19 (3H, d, J=8.0 Hz); HRMS (ESI) calculated for $C_{19}H_{16}ClN_3O_3$ [M+H]$^+$: 370.0880, found 370.0833. 370.0886.

Example 8) Preparation of N-(5-(2-(2-fluorophenyl)acetamido)-2-methylphenyl)-5-methylisoxazole-4-carboxamide

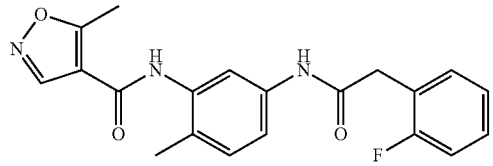 [SMILES: Cc1ccc(NC(=O)Cc2ccccc2F)cc1NC(=O)c1cnoc1C]

white solid, yield: 30%

$^1$H NMR (400 MHz, DMSO) δ 10.22 (1H, s), 9.70 (1H, s), 9.03 (1H, s), 7.67 (1H, d, J=1.6 Hz), 7.40-7.36 (2H, m), 7.34-7.28 (1H, m), 7.19-7.14 (3H, m), 2.66 (3H, s), 2.16 (3H, s); HRMS (ESI) calculated for $C_{20}H_{18}FN_3O_3$ [M+H]$^+$: 368.1332, found 368.1450. 368.1332.

Example 9) Preparation of 5-methyl-N-(2-methyl-5-(3-(2-methyl-1H-imidazol-1-yl)-5-(trifluoromethyl)benzamido)phenyl)isoxazole-4-carboxamide

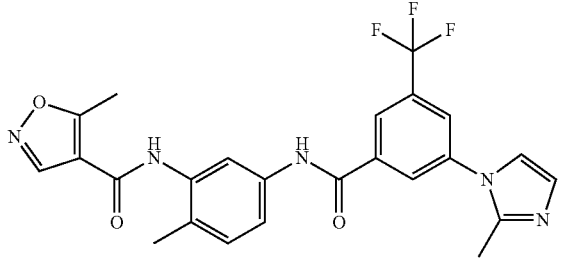 [SMILES: Cc1ccc(NC(=O)c2cc(-n3ccnc3C)cc(C(F)(F)F)c2)cc1NC(=O)c1cnoc1C]

N-(5-amino-2-methylphenyl)-5-methylisoxazole-4-carboxamide (15 mg, 0.065 mmol) prepared in Preparation Example 2, and 3-(2-methyl-imidazol-1-yl)-5-trifluoromethyl-benzoyl chloride (18.76 mg, 0.065 mmol) were added to THF (0.6 mL) and was stirred at 65° C. After completion of the reaction, the reaction mixture was cooled to room temperature, and the solvent was removed by distillation under reduced pressure and purified by column chromatography (silica gel, MC:MeOH=20:1) to give the title compound (yellow solid, 32%).

$^1$H NMR (400 MHz, DMSO) δ 10.82 (1H, s), 9.90 (1H, s), 9.15 (1H, s), 8.54 (2H, s), 8.31 (1H, d, s), 7.99 (1H, s), 7.85 (1H, s), 7.71 (1H, s), 7.65-7.63 (1H, m), 7.28 (1H, d, J=8.4 Hz), 2.67 (3H, s), 2.55 (3H, s), 2.21 (3H, s); HRMS (ESI) calculated for $C_{24}H_{20}F_3N_5O_3$ [M+H]$^+$: 484.1518, found 483.3688. 483.1524.

The following Examples 10 to 18 were prepared in the same manner as in Example 9, except that the compounds corresponding to the structures of the compounds to be prepared were used instead of 3-(2-methyl-imidazol-1-yl)-5-trifluoromethyl-benzoyl chloride.

Example 10) Preparation of 5-methyl-N-(2-methyl-5-(3-(5-methyl-1H-imidazol-1-yl)-5-(trifluoromethyl)benzamido)phenyl)isoxazole-4-carboxamide

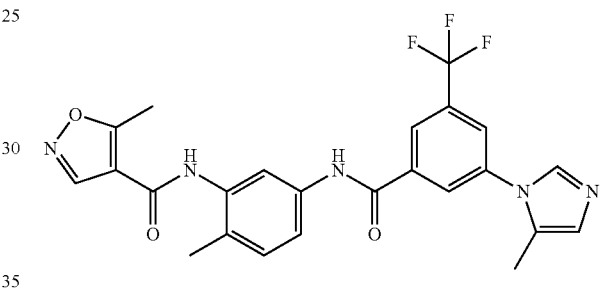

white solid, yield: 22%

$^1$H NMR (400 MHz, DMSO) δ 10.79 (1H, s), 9.88 (1H, s), 9.46 (1H, s), 9.14 (1H, s), 8.60 (2H, d, J=10.8 Hz), 8.41 (1H, s), 7.85 (1H, s), 7.65 (2H, s), 7.29 (1H, d, J=8.0 Hz), 2.67 (3H, s), 2.26 (3H, s), 2.21 (3H, s); HRMS (ESI) calculated for $C_{24}H_{20}F_3N_5O_3$ [M+H]$^+$: 484.1518, found 484.0913. 484.1525.

Example 11) Preparation of 5-methyl-N-(2-methyl-5-(3-(4-methyl-1H-imidazol-1-yl)-5-(trifluoromethyl)benzamido)phenyl)isoxazole-4-carboxamide

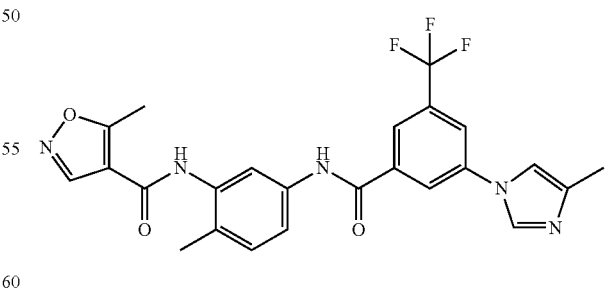

white solid, yield: 32%

$^1$H NMR (400 MHz, DMSO) δ 10.88 (1H, s), 9.88 (1H, s), 9.84 (1H, s), 9.14 (1H, s), 8.77 (1H, s), 8.43 (1H, s), 8.28 (2H, s), 7.89 (1H, s), 7.70 (1H, d, J=8.0 Hz), 7.29 (1H, d, J=8.0 Hz), 2.68 (3H, s), 2.36 (3H, s), 2.22 (3H, s); HRMS (ESI) calculated for $C_{24}H_{20}F_3N_5O_3$ [M+H]$^+$: 484.1518, found 483.0598. 484.1517.

Example 12) Preparation of 5-methyl-N-(2-methyl-5-(quinoline-2-carboxamido)phenyl)isoxazole-4-carboxamide

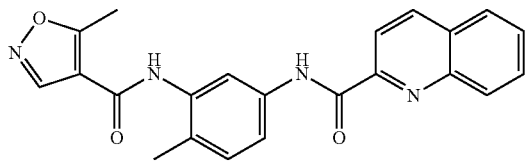 [SMILES: Cc1ccc(NC(=O)c2ccc3ccccc3n2)cc1NC(=O)c1cnoc1C]

white solid, yield: 12%

$^1$H NMR (400 MHz, DMSO) δ 10.76 (1H, s), 9.82 (1H, s), 9.07 (1H, s), 8.64 (1H, d, J=8.4 Hz), 8.26-8.22 (2H, m), 8.14-8.11 (1H, m), 8.04 (1H, d, J=2.4 Hz), 7.94-7.90 (1H, m), 7.78-7.73 (2H, m), 7.31 (1H, d, J=8.8 Hz), 2.69 (3H, s), 2.22 (3H, s); HRMS (ESI) calculated for $C_{22}H_{18}N_4O_3$ [M+H]$^+$: 387.1379, found 387.3237. 387.1382.

Example 13) Preparation of 5-methyl-N-(2-methyl-5-(quinoline-2-carboxamido)phenyl)isoxazole-4-carboxamide

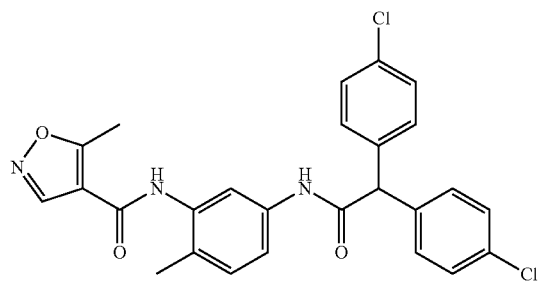 [SMILES: Cc1ccc(NC(=O)C(c2ccc(Cl)cc2)c2ccc(Cl)cc2)cc1NC(=O)c1cnoc1C]

white solid, yield: 12%

$^1$H NMR (400 MHz, DMSO) δ 10.47 (1H, s), 9.69 (1H, s), 9.02 (1H, s), 7.71 (1H, s), 7.41 (4H, d, J=8.4 Hz), 7.35 (5H, d, J=7.2 Hz), 7.19 (1H, d, J=8.4 Hz), 5.17 (1H, s), 2.65 (3H, s), 2.16 (3H, s); HRMS (ESI) calculated for $C_{26}H_{21}Cl_2N_3O_3$ [M+H]$^+$: 494.0960, found 494.0594. 494.0989.

Example 14) Preparation of N-(5-(6-hydroxy-2,5,7,8-tetramethylchroman-2-carboxamido)-2-methylphenyl)-5-methylisoxazole-4-carboxamide

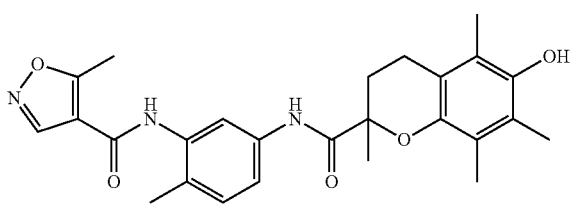 [SMILES: Cc1ccc(NC(=O)C2(C)CCc3c(C)c(O)c(C)c(C)c3O2)cc1NC(=O)c1cnoc1C]

white solid, yield: 9%

$^1$H NMR (400 MHz, DMSO) δ 9.72 (1H, s), 9.21 (1H, s), 9.02 (1H, s), 7.67 (1H, d, J=2.0 Hz), 7.52 (1H, s), 7.36 (1H, dd, J=8.4 Hz, J=2.4 Hz), 7.18 (1H, d, J=8.4 Hz), 2.68 (3H, s), 2.16 (6H, d, J=7.6 Hz), 2.07 (3H, s), 2.05-2.02 (2H, m), 1.99 (3H, d, J=7.2 Hz), 1.50 (3H, d, J=4.8 Hz); HRMS (ESI) calculated for $C_{26}H_{29}N_3O_5$ [M+H]$^+$: 464.2107, found 464.3754. 464.2116.

Example 15) Preparation of N-(5-(1-acetylpiperidine-4-carboxamido)-2-methylphenyl)-5-methyl-isoxazole-4-carboxamide

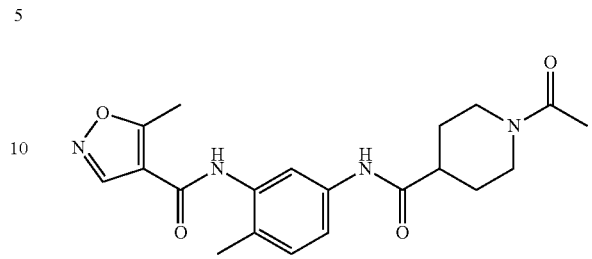

white solid, yield: 20%

$^1$H NMR (400 MHz, DMSO) δ 9.92 (1H, s), 9.70 (1H, s), 9.03 (1H, s), 7.67 (1H, s), 7.37-7.34 (1H, m), 7.17 (1H, d, J=8.4 Hz), 7.24 (1H, s), 7.17 (1H, s), 7.06 (1H, s), 6.99 (1H, d, J=7.2 Hz), 3.71 (2H, s), 3.34 (2H, s), 2.66 (3H, s), 2.15 (3H, s), 2.00 (3H, s), 1.84 (2H, s); HRMS (ESI) calculated for $C_{20}H_{24}N_4O_4$ [M+H]$^+$: 385.1798, found 385.3514. 385.1805.

Example 16) Preparation of N-(5-(2-(1H-indol-3-yl)acetamido)-2-methylphenyl)-5-methylisoxazole-4-carboxamide

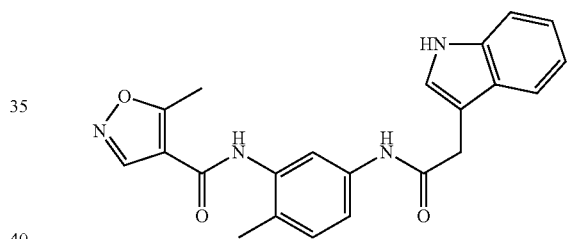

white solid, yield: 17%

$^1$H NMR (400 MHz, DMSO) δ 10.88 (1H, s), 10.06 (1H, s), 9.67 (1H, s), 9.01 (1H, s), 7.66-7.58 (2H, m), 7.33 (2H, s), 7.24 (1H, s), 7.17 (1H, s), 7.06 (1H, s), 6.99 (1H, d, J=7.2 Hz), 3.71 (2H, s), 2.66 (3H, s), 2.15 (3H, s); HRMS (ESI) calculated for $C_{22}H_{20}N_4O_3$ [M+H]$^+$: 389.1535, found 389.3299. 389.1539.

Example 17) Preparation of 5-methyl-N-(2-methyl-5-(pyrazine-2-carboxamido)phenyl)isoxazole-4-carboxamide

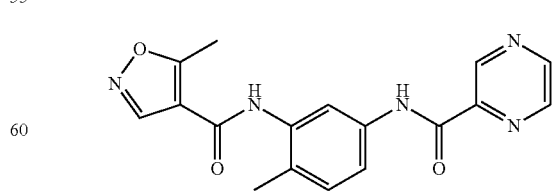

white solid, yield: 30%

$^1$H NMR (400 MHz, DMSO) δ 9.91 (1H, s), 9.13 (1H, s), 9.01 (1H, s), 7.40-7.31 (2H, m), 7.13 (1H, d, J=8.4 Hz), 2.67-2.64 (3H, m), 2.24-2.21 (3H, m); HRMS (ESI) calculated for $C_{17}H_{15}N_5O_3$ [M+H]$^+$: 338.1175, found 338.3225. 338.1184.

Example 18) Preparation of N-(5-(1H-benzo[d][1,2,3]triazole-5-carboxamido)-2-methylphenyl)-5-methylisoxazole-4-carboxamide

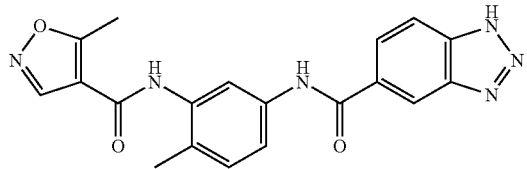 [SMILES: Cc1ccc(NC(=O)c2ccc3[nH]nnc3c2)cc1NC(=O)c1cnoc1C]

white solid, yield: 24%

$^1$H NMR (400 MHz, DMSO) δ 9.80 (1H, s), 9.67 (1H, s), 9.01 (1H, s), 7.66-7.58 (2H, m), 7.42 (1H, s), 7.35-7.30 (2H, m), 7.07 (1H, d, J=8.0 Hz), 2.67 (3H, s), 2.22 (3H, d, J=9.6 Hz); HRMS (ESI) calculated for $C_{19}H_{16}N_6O_3$ [M+H]$^+$: 377.1284, found 377.3264. 377.1284.

Example 19) Preparation of N-(5-(indoline-2-carboxamido)-2-methylphenyl)-5-methylisoxazole-4-carboxamide

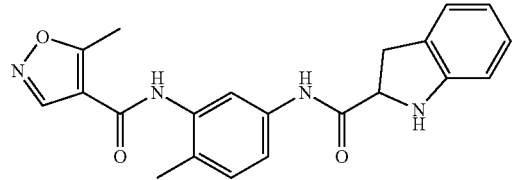 [SMILES: Cc1ccc(NC(=O)C2Cc3ccccc3N2)cc1NC(=O)c1cnoc1C]

N-(5-amino-2-methylphenyl)-5-methylisoxazole-4-carboxamide (20 mg, 0.086 mmol) prepared in Preparation Example 2, and 2,3-dihydro-1H-indole-carbonyl chloride (15.62 mg, 0.086 mmol) were added to THF (0.8 mL) and stirred at 65° C. After completion of the reaction, the reaction mixture was cooled to room temperature, and the solvent was removed by distillation under reduced pressure and purified by column chromatography (silica gel, MC:MeOH=20:1) to give the title compound (white solid, 12%).

$^1$H NMR (400 MHz, DMSO) δ 10.02 (1H, s), 9.17 (1H, s), 9.09 (1H, s), 7.62 (1H, s), 7.55-7.49 (2H, m), 7.47-7.41 (4H, m), 2.67 (3H, s), 2.20 (3H, s); HRMS (ESI) calculated for $C_{21}H_{20}N_4O_3$ [M+H]$^+$: 377.1535, found 377.2583. 377.1533.

The following Examples 20 to 27 were prepared in the same manner as in Example 19, except that the compounds corresponding to the structures of the compounds to be prepared were used instead of 2,3-dihydro-1H-indole-2-carbonyl chloride.

Example 20) Preparation of N-(5-(isonicotinamido)-2-methylphenyl)-5-methylisoxazole-4-carboxamide

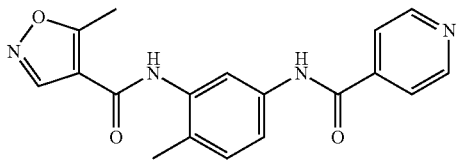 [SMILES: Cc1ccc(NC(=O)c2ccncc2)cc1NC(=O)c1cnoc1C]

white solid, yield: 7/%

$^1$H NMR (400 MHz, DMSO) δ 10.51 (1H, s), 9.78 (1H, s), 9.05 (1H, s), 8.79-8.77 (2H, m), 7.86-7.85 (3H, m), 7.58-7.56 (1H, m), 7.27 (1H, d, J=8.4 Hz), 2.68 (3H, s), 2.20 (3H, s); HRMS (ESI) calculated for $C_{18}H_{16}N_4O_3$ [M+H]$^+$: 337.1222, found 337.1323. 359.1224 (Na$^+$).

Example 21) Preparation of N-(5-(2-(2-cyanophenylthio)benzamido)-2-methylphenyl)-5-methylisoxazole-4-carboxamide

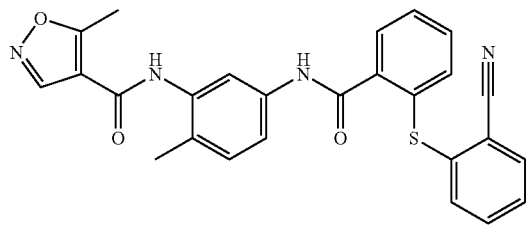 [SMILES: Cc1ccc(NC(=O)c2ccccc2Sc2ccccc2C#N)cc1NC(=O)c1cnoc1C]

white solid, yield: 52%

$^1$H NMR (400 MHz, DMSO) δ 10.51 (1H, s), 9.80 (1H, s), 9.03 (1H, s), 7.91 (1H, s), 7.81 (1H, s), 7.72-7.65 (2H, m), 7.52-7.39 (5H, m), 7.24 (2H, d, J=8.0 Hz), 7.18-7.15 (1H, m), 2.67 (3H, s), 2.18 (3H, s); HRMS (ESI) calculated for $C_{26}H_{20}N_4O_3S$ [M+H]$^+$: 469.1256, found 469.0677. 469.1261.

Example 22) Preparation of N-(5-(2-(biphenyl-4-yl)acetamido)-2-methylphenyl)-5-methylisoxazole-4-carboxamide

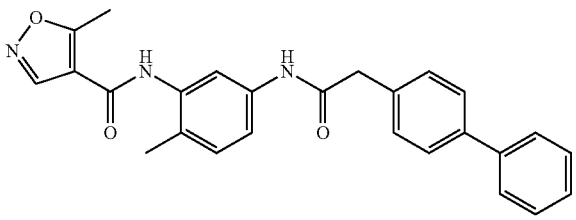 [SMILES: Cc1ccc(NC(=O)Cc2ccc(-c3ccccc3)cc2)cc1NC(=O)c1cnoc1C]

white solid, yield: 30%

$^1$H NMR (400 MHz, DMSO) δ 10.21 (1H, s), 9.70 (1H, s), 9.03 (1H, s), 7.67-7.61 (5H, m), 7.47-7.33 (6H, m), 7.19 (1H, d, J=8.0 Hz), 3.66 (2H, d, J=8.0 Hz), 2.68 (3H, d, J=8.0 Hz), 2.16 (3H, d, J=7.6 Hz); HRMS (ESI) calculated for $C_{26}H_{23}N_3O_3$ [M+H]$^+$: 426.1739, found 426.1245. 426.1740.

Example 23) Preparation of 5-methyl-N-(2-methyl-5-(1-phenyl-5-(trifluoromethyl)-1H-pyrazole-4-carboxamido)phenyl)isoxazole-4-carboxamide

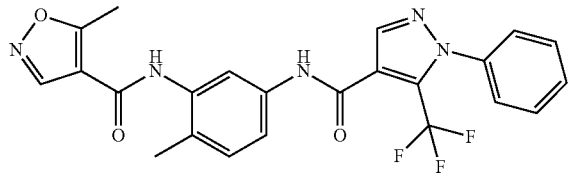 [SMILES: Cc1ccc(NC(=O)c2cnn(-c3ccccc3)c2C(F)(F)F)cc1NC(=O)c1cnoc1C]

white solid, yield: 74%

$^1$H NMR (400 MHz, DMSO) δ 10.53 (1H, s), 9.79 (1H, s), 9.05 (1H, s), 8.31 (1H, s), 7.80 (1H, s), 7.62-7.60 (3H, m), 7.54-7.53 (2H, m), 7.47 (1H, d, J=8.0 Hz), 7.26 (1H, d, J=8.4 Hz), 2.68 (3H, s), 2.19 (3H, d, J=8.0 Hz); HRMS (ESI) calculated for $C_{23}H_{18}F_3N_5O_3$ [M+H]$^+$: 470.1362, found 470.0538. 470.1365.

Example 24) Preparation of N-(5-(3,5-dimethylbenzamido)-2-methylphenyl)-5-methylisoxazole-4-carboxamide

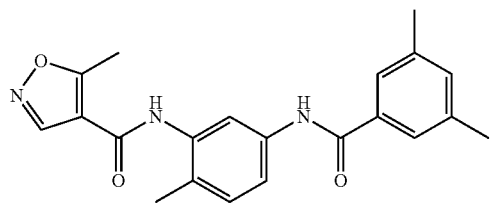 [SMILES: Cc1cc(C)cc(C(=O)Nc2ccc(C)c(NC(=O)c3cnoc3C)c2)c1]

white solid, yield: 53%

$^1$H NMR (400 MHz, DMSO) δ 10.16 (1H, d, J=7.6 Hz), 9.78 (1H, s), 9.06 (1H, s), 7.83 (1H, d, J=6.0 Hz), 7.57-7.54 (3H, m), 7.24 (2H, m), 2.68 (3H, s), 2.35 (6H, d, J=8.4 Hz), 2.19 (3H, d, J=8.0 Hz); HRMS (ESI) calculated for $C_{21}H_{21}N_3O_3$ [M+H]$^+$: 364.1583, found 364.1226. 364.1587.

Example 25) Preparation of N-(5-biphenyl-2-ylcarboxamido-2-methylphenyl)-5-methylisoxazole-4-carboxamide

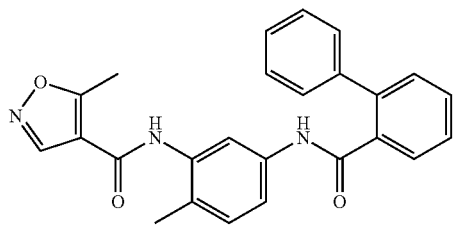 [SMILES: Cc1ccc(NC(=O)c2ccccc2-c2ccccc2)cc1NC(=O)c1cnoc1C]

white solid, yield: 20%

$^1$H NMR (400 MHz, DMSO) δ 10.31 (1H, d, J=8 Hz), 9.79 (1H, d, J=8 Hz), 9.06 (1H, s), 8.05 (2H, s), 7.85 (3H, d, J=8 Hz), 7.75 (2H, s), 7.59 (1H, s), 7.50 (2H, d, J=3.2 Hz), 7.42 (1H, s), 7.24 (1H, s), 2.68 (3H, d, J=8.8 Hz), 2.20 (3H, d, J=8.8 Hz); HRMS (ESI) calculated for $C_{26}H_{23}N_3O_3$ [M+H]$^+$: 412.1583, found 412.0786. 412.1583.

Example 26) Preparation of N-(5-biphenyl-4-ylcarboxamido-2-methylphenyl)-5-methylisoxazole-4-carboxamide

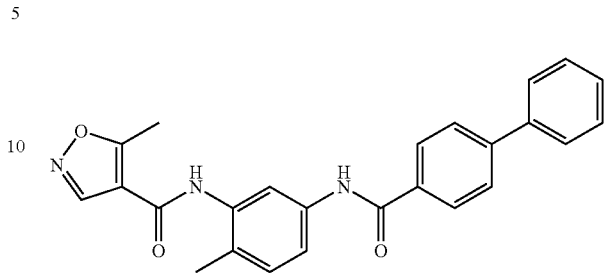

white solid, yield: 14%

$^1$H NMR (400 MHz, DMSO) δ 10.23 (1H, s), 9.73 (1H, s), 9.00 (1H, s), 7.62 (1H, s), 7.55-7.54 (2H, m), 7.49-7.41 (4H, m), 7.38-7.35 (2H, m), 7.30-7.24 (1H, m) 7.15-7.12 (1H, m), 2.65 (3H, d, J=3.2 Hz), 2.20 (3H, d, J=2.8 Hz); HRMS (ESI) calculated for $C_{26}H_{23}N_3O_3$ [M+H]$^+$: 412.1583, found 412.1126. 412.1590.

Example 27) Preparation of 5-methyl-N-(2-methyl-5-(quinoline-3-carboxamido)phenyl)isoxazole-4-carboxamide

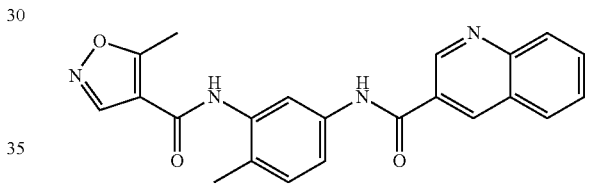

white solid, yield: 9%

$^1$H NMR (400 MHz, DMSO) δ 10.60 (1H, s), 9.76 (1H, s), 9.35 (1H, d, J=2.0 Hz), 9.06 (1H, s), 8.96 (1H, s), 8.13 (3H, s), 7.90 (2H, s), 7.72 (1H, s), 7.64 (1H, d, J=7.2 Hz), 2.68 (3H, s), 2.22 (3H, s); HRMS (ESI) calculated for $C_{22}H_{18}N_4O_3$ [M+H]$^+$: 387.1379, found 387.2556. 387.1379.

Example 28) Preparation of N-(5-(3-(4-chlorophenyl)ureido)-2-methylphenyl)-5-methylisoxazole-4-carboxamide

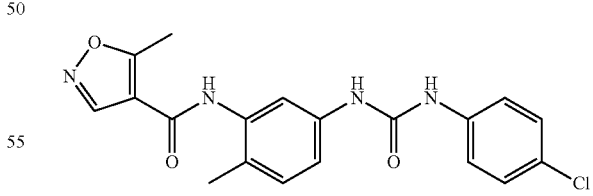

N-(5-amino-2-methylphenyl)-5-methylisoxazole-4-carboxamide (10 mg, 0.043 mmol) prepared in Preparation Example 2, and 4-chlorophenyl isocyanate (6.7 mg, 0.043 mmol) were added to THF (0.4 mL) and stirred at room temperature. After completion of the reaction, the solvent was removed by distillation under reduced pressure and the residue was purified by column chromatography (silica gel, MC:MeOH=20:1) to give the title compound (white solid, 30%).

¹H NMR (400 MHz, DMSO) δ 9.75 (1H, s), 9.35 (1H, s), 9.11 (1H, s), 9.03 (1H, s), 8.06 (1H, s), 7.84-7.58 (5H, m), 7.23 (1H, s), 2.67 (3H, s), 2.15 (3H, s); HRMS (ESI) calculated for $C_{19}H_{17}ClN_4O_3$ [M+H]⁺: 385.0989, found 385.1133. 407.0978 (Na⁺).

The following Examples 29 to 34 were prepared in the same manner as in Example 28, except that the compounds corresponding to the structures of the compounds to be prepared were used instead of 4-chlorophenyl isocyanate.

Example 29) Preparation of 5-methyl-N-(2-methyl-5-(3-(3-(trifluoromethyl)phenyl)ureido)phenyl)isoxazole-4-carboxamide

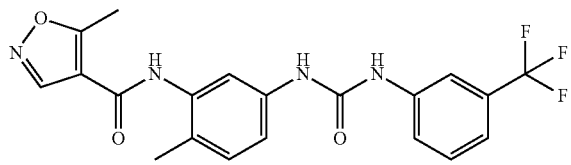 [SMILES: Cc1ccc(NC(=O)Nc2cccc(C(F)(F)F)c2)cc1NC(=O)c1cnoc1C]

pale yellow solid, yield: 37%

¹H NMR (400 MHz, DMSO) δ 9.75 (1H, s), 9.38 (1H, s), 9.11 (1H, s), 9.06 (1H, s), 8.01 (1H, s), 7.94 (2H, s), 7.55 (1H, s), 7.51-7.48 (1H, m), 7.30 (1H, d, J=7.6 Hz), 7.23-7.15 (1H, m), 2.67 (3H, s), 2.15 (3H, s); HRMS (ESI) calculated for $C_{20}H_{17}F_3N_4O_3$ [M+H]⁺: 419.1253, found 419.1513. 419.1258.

Example 30) Preparation of N-(5-(3-(4-chloro-3-(trifluoromethyl)phenyl)ureido)-2-methylphenyl)-5-methylisoxazole-4-carboxamide

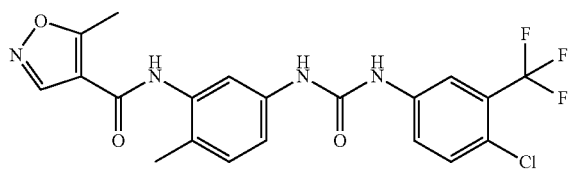 [SMILES: Cc1ccc(NC(=O)Nc2ccc(Cl)c(C(F)(F)F)c2)cc1NC(=O)c1cnoc1C]

pale yellow solid, yield: 44%

¹H NMR (400 MHz, DMSO) δ 9.71 (1H, s), 9.10 (1H, s), 9.03 (1H, s), 8.85 (1H, s), 8.12 (1H, s), 7.60-7.56 (3H, m), 7.19 (2H, s), 2.67 (3H, s), 2.16 (3H, s); HRMS (ESI) calculated for $C_{20}H_{16}ClF_3N_4O_3$ [M+H]⁺: 453.0863, found 453.1885. 453.0866.

Example 31) Preparation of N-(5-(3-(2-fluorophenyl)ureido)-2-methylphenyl)-5-methylisoxazole-4-carboxamide

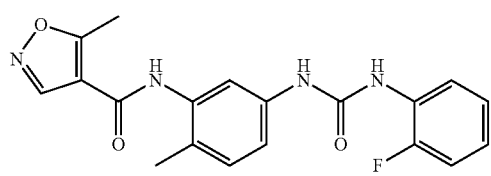 [SMILES: Cc1ccc(NC(=O)Nc2ccccc2F)cc1NC(=O)c1cnoc1C]

Pale yellow solid, yield: 25%

¹H NMR (400 MHz, DMSO) δ 9.71 (1H, s), 9.05 (1H, s), 8.93 (1H, s), 8.80 (1H, s), 7.65-7.02 (7H, m), 2.67 (3H, s), 2.16 (3H, s); HRMS (ESI) calculated for $C_{19}H_{17}FN_4O_3$ [M+H]⁺: 369.1285, found 369.1312. 369.1291.

Example 32) Preparation of N-(5-(3-(3-chlorophenyl)ureido)-2-methylphenyl)-5-methylisoxazole-4-carboxamide

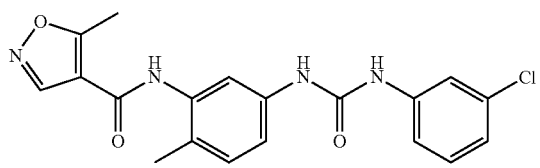 [SMILES: Cc1ccc(NC(=O)Nc2cccc(Cl)c2)cc1NC(=O)c1cnoc1C]

white solid, yield: 21%

¹H NMR (400 MHz, DMSO) δ 9.70 (1H, s), 9.03 (1H, s), 8.84 (1H, s), 8.76 (1H, s), 7.70 (1H, s), 7.55 (1H, s), 7.30-7.23 (3H, m), 7.18 (1H, d, J=5.6 Hz), 7.01 (1H, d, J=6 Hz), 2.67 (3H, s), 2.15 (3H, s); HRMS (ESI) calculated for $C_{19}H_{17}ClN_4O_3$ [M+H]⁺: 385.0989, found 385.0453. 385.0984.

Example 33) Preparation of N-(5-(3-(3,5-dichlorophenyl)ureido)-2-methylphenyl)-5-methylisoxazole-4-carboxamide

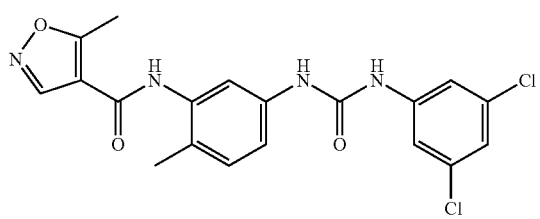 [SMILES: Cc1ccc(NC(=O)Nc2cc(Cl)cc(Cl)c2)cc1NC(=O)c1cnoc1C]

white solid, yield: 16%

¹H NMR (400 MHz, DMSO) δ 9.71 (1H, s), 9.03 (2H, d, J=7.2 Hz), 8.90 (1H, s), 7.55 (1H, s), 7.52 (1H, d, J=1.6 Hz), 7.19-7.15 (3H, m), 2.67 (3H, s), 2.15 (3H, s); HRMS (ESI) calculated for $C_{19}H_{16}Cl_2N_4O_3$ [M+H]⁺: 419.0599, found 419.0153. 441.0591 (Na⁺).

Example 34) Preparation of N-(5-(3-(3,4-dichlorophenyl)ureido)-2-methylphenyl)-5-methylisoxazole-4-carboxamide

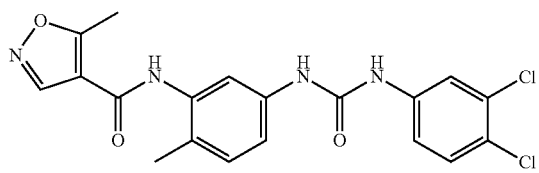 [SMILES: Cc1ccc(NC(=O)Nc2ccc(Cl)c(Cl)c2)cc1NC(=O)c1cnoc1C]

white solid, yield: 23%

¹H NMR (400 MHz, DMSO) δ 9.70 (1H, s), 9.13-8.81 (3H, m), 7.87 (1H, d, J=6.4 Hz), 7.53 (2H, d, J=9.6 Hz), 7.33 (2H, d, J=8.0 Hz), 7.18 (1H, d, J=2.0 Hz), 2.66 (3H, s), 2.15 (3H, s); HRMS (ESI) calculated for $C_{19}H_{16}Cl_2N_4O_3$ [M+H]⁺: 419.0599, found 419.0493. 419.0595.

Example 35) Preparation of N-(4-(3-(4-chloro-3-(trifluoromethyl)phenyl)ureido)-2-methylphenyl)-5-methylisoxazole-4-carboxamide

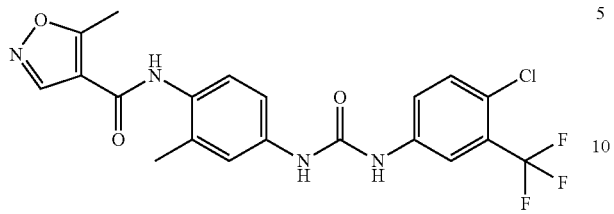

N-(4-amino-2-methylphenyl)-5-methylisoxazole-4-carboxamide (20 mg, 0.086 mmol) prepared in Preparation Example 1 and 4-chloro-3-(trifluoromethyl)phenyl isocyanate (19.05 mg, 0.086 mmol) were added to THF (0.8 mL) and stirred at room temperature. After completion of the reaction, the solvent was removed by distillation under reduced pressure and the residue was purified by column chromatography (silica gel, MC:MeOH=20:1) to give the title compound (white solid, 49%).

$^1$H NMR (400 MHz, DMSO) δ 9.63 (1H, s), 9.15 (1H, s), 9.02 (1H, s), 8.81 (1H, s), 8.12 (1H, s), 7.61 (2H, s), 7.38 (1H, s), 7.29 (1H, d, J=6.0 Hz), 7.20 (1H, s), 2.66 (3H, s), 2.18 (3H, s); HRMS (ESI) calculated for $C_2H_{16}ClF_3N_4O_3$ [M+H]$^+$: 453.0863, found 453.0186. 453.0865.

The following Examples 36 to 41 are prepared in the same manner as in Example 35, except that the compounds corresponding to the structures of the compounds to be prepared were used instead of 4-chloro-3-(trifluoromethyl)phenyl isocyanate.

Example 36) Preparation of 5-methyl-N-(2-methyl-4-(3-(3-(trifluoromethyl)phenyl)ureido)phenyl)isoxazole-4-carboxamide

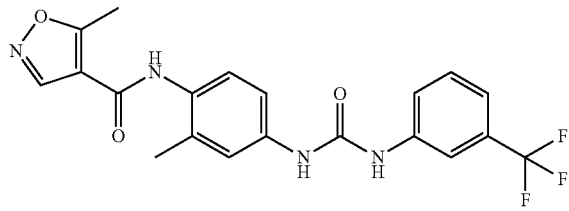 [SMILES: Cc1cc(NC(=O)Nc2cccc(C(F)(F)F)c2)ccc1NC(=O)c1cnoc1C]

white solid, yield: 42%

$^1$H NMR (400 MHz, DMSO) δ 9.64 (1H, s), 9.04 (2H, d, J=4.8 Hz), 8.77 (1H, s), 8.03 (1H, s), 7.57-7.49 (2H, m), 7.39 (1H, d, J=2.4 Hz), 7.31-7.28 (2H, m), 7.20 (1H, d, J=8.4 Hz), 2.66 (3H, s), 2.19 (3H, s); HRMS (ESI) calculated for $C_{20}H_{17}F_3N_4O_3$ [M+H]$^+$: 419.1253, found 419.1173. 419.1252.

Example 37) Preparation of N-(4-(3-(3-chlorophenyl)ureido)-2-methylphenyl)-5-methylisoxazole-4-carboxamide

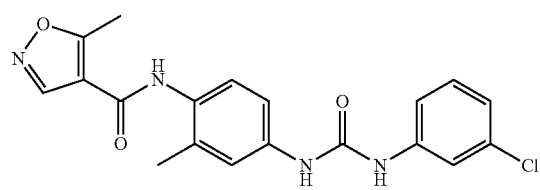 [SMILES: Cc1cc(NC(=O)Nc2cccc(Cl)c2)ccc1NC(=O)c1cnoc1C]

white solid, yield: 66%

$^1$H NMR (400 MHz, DMSO) δ 9.63 (1H, s), 9.03 (1H, s), 8.93 (1H, s), 8.76 (1H, s), 7.71 (1H, s), 7.37 (1H, s), 7.29 (2H, d, J=6.4 Hz), 7.19 (2H, d, J=4.8 Hz), 7.01 (2H, d, J=4.0 Hz), 2.66 (3H, s), 2.18 (3H, s); HRMS (ESI) calculated for $C_{19}H_{17}ClN_4O_3$ [M+H]$^+$: 385.0989, found 385.0793. 407.0981 (Na$^+$).

Example 38) Preparation of N-(4-(3-(2-fluorophenyl)ureido)-2-methylphenyl)-5-methylisoxazole-4-carboxamide

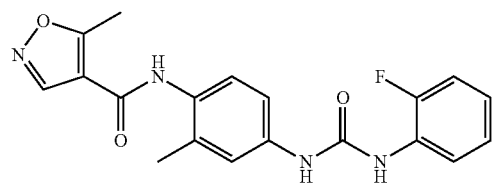 [SMILES: Cc1cc(NC(=O)Nc2ccccc2F)ccc1NC(=O)c1cnoc1C]

white solid, yield: 53%

$^1$H NMR (400 MHz, DMSO) δ 9.64 (1H, s), 9.05 (2H, d, J=5.2 Hz), 8.55 (1H, s), 8.15 (1H, s), 7.36 (1H, s), 7.28 (1H, s), 7.23 (2H, d, J=9.2 Hz), 7.13 (1H, s), 7.00 (1H, s), 2.67 (3H, s), 2.19 (3H, s); HRMS (ESI) calculated for $C_{19}H_{17}FN_4O_3$ [M+H]$^+$: 369.1285, found 369.0972. 369.1280.

Example 39) Preparation of N-(4-(3-(4-chlorophenyl)ureido)-2-methylphenyl)-5-methylisoxazole-4-carboxamide

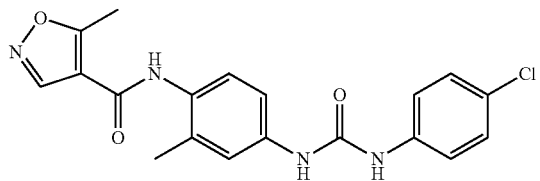 [SMILES: Cc1cc(NC(=O)Nc2ccc(Cl)cc2)ccc1NC(=O)c1cnoc1C]

white solid, yield: 63%

$^1$H NMR (400 MHz, DMSO) δ 9.68 (1H, s), 9.38 (1H, s), 9.20 (1H, s), 9.07 (1H, s), 7.49 (2H, dd, J=2.4 Hz, J=2.4 Hz), 7.34-7.28 (4H, m), 7.17 (1H, d, J=8.8 Hz), 2.65 (3H, s), 2.17 (3H, s); HRMS (ESI) calculated for $C_{19}H_{17}ClN_4O_3$ [M+H]$^+$: 385.0989, found 385.1133. 407.0982 (Na$^+$).

Example 40) Preparation of N-(4-(3-(3,4-dichlorophenyl)ureido)-2-methylphenyl)-5-methylisoxazole-4-carboxamide

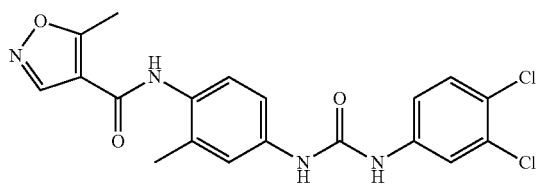 [SMILES: Cc1cc(NC(=O)Nc2ccc(Cl)c(Cl)c2)ccc1NC(=O)c1cnoc1C]

white solid, yield: 42%

$^1$H NMR (400 MHz, DMSO) δ 9.63 (1H, s), 9.02 (2H, s), 8.80 (1H, s), 7.88 (1H, s), 7.51 (1H, d, J=7.2 Hz), 7.36 (1H, s), 7.32-7.27 (2H, m), 7.19 (1H, s), 2.65 (3H, s), 2.18 (3H,

Example 41) Preparation of N-(4-(3-(3,5-dichlorophenyl)ureido)-2-methylphenyl)-5-methylisoxazole-4-carboxamide

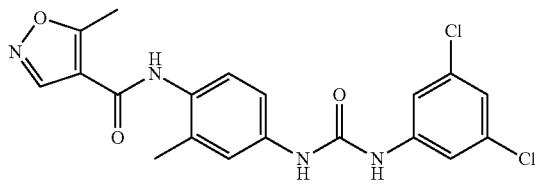 [SMILES: Cc1cc(NC(=O)Nc2cc(Cl)cc(Cl)c2)ccc1NC(=O)c1cnoc1C]

white solid, yield: 38%
$^1$H NMR (400 MHz, DMSO) δ 9.87 (1H, s), 9.70 (1H, s), 9.38 (1H, s), 9.08 (1H, s), 7.52 (2H, s), 7.35 (1H, s), 7.28 (1H, s), 7.19 (1H, s), 7.14 (1H, s), 2.66 (3H, s), 2.18 (3H, s); HRMS (ESI) calculated for $C_{19}H_{16}Cl_2N_4O_3$ [M+H]$^+$: 419.0599, found 419.2533. 419.0591.

Example 42) Preparation of 5-methyl-N-(2-methyl-5-(propylsulfonamido)phenyl)isoxazole-4-carboxamide

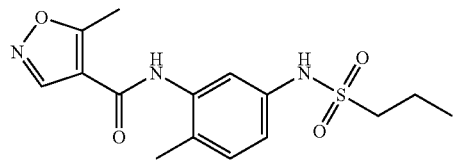 [SMILES: CCCS(=O)(=O)Nc1ccc(C)c(NC(=O)c2cnoc2C)c1]

N-(4-amino-2-methylphenyl)-5-methylisoxazole-4-carboxamide (20 mg, 0.086 mmol) prepared in Preparation Example 1, propane-1-sulfonyl chloride (19.05 mg, 0.095 mmol) and pyridine were added to MC (0.4 mL) and stirred at room temperature. After completion of the reaction, the solvent was removed by distillation under reduced pressure and the residue was purified by column chromatography (silica gel, EA:Hexane=1:1) to give the title compound (white solid, 47%).
$^1$H NMR (400 MHz, DMSO) δ 9.75 (1H, s), 9.66 (1H, s), 9.01 (1H, s), 7.24 (1H, d, J=8.4 Hz), 7.09-7.04 (3H, m), 3.07-3.04 (2H, m), 2.65 (3H, s), 2.17 (3H, s), 1.69 (2H, d, J=7.2 Hz), 0.93 (3H, s); HRMS (ESI) calculated for $C_{15}H_{19}N_3O_4S$ [M+H]$^+$: 338.1096, found 338.2801. 338.1090.

Example 43) Preparation of 5-methyl-N-(2-methyl-4-(propylsulfonamido)phenyl)isoxazole-4-carboxamide

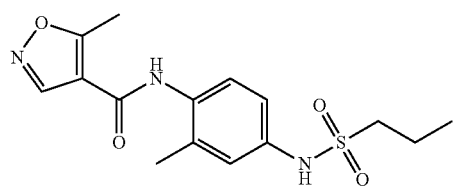 [SMILES: CCCS(=O)(=O)Nc1ccc(NC(=O)c2cnoc2C)c(C)c1]

N-(5-amino-2-methylphenyl)-5-methylisoxazole-4-carboxamide (20 mg, 0.086 mmol) prepared in Preparation Example 2, propane-1-sulfonyl chloride (19.05 mg, 0.095 mmol) and pyridine were added to MC (0.4 mL) and stirred at room temperature. After completion of the reaction, the solvent was removed by distillation under reduced pressure and the residue was purified by column chromatography (silica gel, EA:Hexane=1:1) to give the title compound (white solid, 44%).
$^1$H NMR (400 MHz, DMSO) δ 9.74 (2H, s), 9.02 (1H, s), 9.01 (1H, s), 7.20 (2H, s), 7.03 (1H, d, J=8.0 Hz), 3.03 (2H, s), 2.66 (3H, s), 2.15 (3H, s), 1.68-1.66 (2H, m), 0.93 (3H, s); HRMS (ESI) calculated for $C_{15}H_{19}N_3O_4S$ [M+H]$^+$: 338.1096, found 338.1524. 338.1094.

Example 44) Preparation of 5-methyl-N-(2-methyl-5-(3-morpholino-5-(trifluoromethyl)benzamido)phenyl)isoxazole-4-carboxamide The title compound (white solid, 53.4%) was obtained in the same manner as in Example 3, except that 3-morpholino-5-(trifluoromethyl)benzoic acid was used instead of 3-(4-methyl-piperazin-1-yl)-5-trifluoromethylbenzoic acid.
$^1$H NMR (400 MHz, DMSO) δ 10.37 (1H, s), 9.78 (1H, s), 9.06 (1H, s), 7.81 (1H, d, J=2.1 Hz), 7.72 (1H, s), 7.65 (1H, s), 7.60-7.57 (1H, dd, J=8.3, 2.2 Hz), 7.39 (1H, s), 7.27-7.25 (1H, d, J=8.5 Hz) 3.78-3.76 (4H, m), 3.35-3.28 (4H, m), 2.68 (3H, s), 2.21 (3H, s); HRMS (ESI) calculated for $C_{24}H_{23}F_3N_4O_4$ [M+H]$^+$, found 489.0081. 489.0396.

Experimental Example 1) Measurement of A375P Cell Line Proliferation Inhibitory Activity A375P cell lines were purchased from ATCC and cultured in a DMEM culture medium (containing 10% FBS and 1% penicillin/streptomycin) in the presence of 5% $CO_2$ at 37° C. The cultured A375P cell lines were taken from culture substrate with 0.05% trypsin-0.02% EDTA and plated at a density of $5 \times 10^3$ cells per well in 96-well plates.

In order to measure cell viability, MTT [3-(4,5-dimethylthiazole-2-yl)-2,5-diphenyltetrazolium bromide] activity assay method (Thiazolyl Blue Tetrazolium Bromide, Sigma Aldrich) was used. Cell lines were cultured in 96-well plates for 24 hours and treated with the compounds of Examples previously prepared. For the compound treatment, 10 mM stocks were prepared, serially diluted in DMSO and added by 0.5 μL at 8 points (final concentration of 0.5%). The cell lines in plates treated with the compounds was cultured for 48 hours, then 15 μL of dye was added to each well and cultured for 4 hours. Then, 100 μL of DMSO solvent was added to each well, and the formed solid was dissolved to measure the absorbance. The absorbance was read at a wavelength of 570 nm using EnVision 2103, and the GI 50 value was calculated using GraphPad Prism 4.0 software, and the results are shown in Table 1 below.

TABLE 1

| Example No. | A375P |
| --- | --- |
| 1 | + |
| 2 | + |
| 3 | + |
| 4 | + |
| 5 | + |
| 6 | + |
| 7 | + |
| 8 | + |

TABLE 1-continued

| Example No. | A375P |
|---|---|
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | ++ |
| 41 | + |
| 42 | + |
| 43 | + |
| 44 | + |
| Sorafenib | 2.74 μM |

$GI_{50}$: 10~30 μM: (+)
$GI_{50}$: 1~10 μM: (++)
$GI_{50}$: <1 μM: (+++)

Experimental Example 2) Measurement of U937 Cell Line Proliferation Inhibitory Activity U937 cell lines were purchased from ATCC and cultured in a RPMI culture medium (containing 10% FBS, 1% penicillin/streptomycin and 25 mM HEPES) in the presence of 5% $CO_2$ at 37° C. The cell line proliferation inhibitory activity for Examples previously prepared was measured using the same MTT activity assay method as the A375P cell line proliferation inhibitory activity assay in Experimental Example 1. The results are shown in Table 2 below.

TABLE 2

| Example No. | U937 |
|---|---|
| 1 | + |
| 2 | + |
| 3 | +++ |
| 4 | +++ |
| 5 | + |
| 6 | + |
| 7 | + |
| 8 | + |
| 9 | +++ |
| 10 | +++ |
| 11 | +++ |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | +++ |
| 24 | ++ |
| 25 | + |
| 26 | + |
| 27 | + |
| 28 | + |
| 29 | + |
| 30 | + |
| 31 | + |
| 32 | + |
| 33 | + |
| 34 | ++ |
| 35 | + |
| 36 | + |
| 37 | + |
| 38 | + |
| 39 | + |
| 40 | + |
| 41 | + |
| 42 | + |
| 43 | + |
| 44 | +++ |
| Sorafenib | 2.74 μM |

$GI_{50}$: 10~30 μM: (+)
$GI_{50}$: 1~10 μM: (++)
$GI_{50}$: <1 μM: (+++)

Experimental Example 3) Measurement of FMS Inhibitory Activity

The inhibitory activity of FMS at a concentration of 10 μM of the compound prepared in Example 5 was measured using Kinase profiling services (IC 50 profiler express) offered by Reaction Biology Corporation. As a result, it was confirmed that the FMS activity was inhibited by 98.7%. In addition, it was confirmed that the concentration that inhibits FMS activity by 50% ($IC_{50}$) while sequentially decreasing the concentration of the compound was 9.95 nM.

The invention claimed is:

1. A compound represented by the following Chemical Formula 1, or a pharmaceutically acceptable salt thereof:

[Chemical Formula 1]

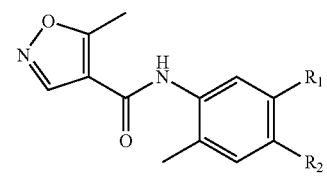

wherein:
$R_1$ is hydrogen and $R_2$ is $R_3$, or $R_1$ is $R_3$ and $R_2$ is hydrogen,
$R_3$ is —NHCO—$R_4$, —NHCONH—$R_5$, or —NHSO$_2$—$R_6$;
$R_4$ is (1H-indol-3-yl)methyl; 1-acetylpiperidin-4-yl; 1-phenyl-5-(trifluoromethyl)-1H-pyrazolyl; 6-hydroxy-2,5,7,8-tetramethylchroman-2-yl; benzotriazolyl; biphenyl; di(4-chlorophenyl)methyl; indolinyl; pyrazinyl; pyridinyl; quinolinyl; phenyl substituted with one or two substituents each independently selected from the group consisting of $C_{1-4}$ alkyl, $C_{1-4}$ haloalkyl, halogen, morpholino, imidazolyl substituted with methyl, piperazinyl substituted with methyl, and cyanophenylthio; or benzyl substituted with halogen or phenyl, $R_5$ is phenyl substituted with one or two substituents each independently selected from the group consisting of $C_{1-4}$ haloalkyl and halogen, and $R_6$ is $C_{1-4}$ alkyl.

2. The compound or a pharmaceutically acceptable salt thereof according to claim 1, wherein $R_4$ is (1H-indol-3-yl)methyl; 1-acetylpiperidin-4-yl; phenyl-5-(trifluoromethyl)-1H-pyrazolyl; 6-hydroxy-2,5,7,8-tetramethylchroman-2-yl; 1H-benzo[d][1,2,3]triazol-5-yl; biphenyl-2-yl, biphenyl-4-yl; di(4-chlorophenyl)methyl; indolin-2-yl; pyrazin-2-yl; pyridin-4-yl; quinolin-2-yl; quinolin-3-yl; phenyl substituted by one or two substituents each independently selected from the group consisting of methyl, trifluoromethyl, chloro, morpholino, 2-methyl-1H-imidazol-1-yl, 4-methyl-1H-imidazol-1-yl, 5-methyl-1H-imidazole-1-yl, 4-methylpiperazin-1-yl and cyanophenylthio; or benzyl substituted with fluoro or phenyl.

3. The compound or a pharmaceutically acceptable salt thereof according to claim 1, wherein $R_5$ is phenyl substituted with one or two substituents each independently selected from the group consisting of trifluoromethyl, fluoro and chloro.

4. The compound or a pharmaceutically acceptable salt thereof according to claim 1, wherein $R_6$ is propyl.

5. The compound or a pharmaceutically acceptable salt thereof according to claim 1, wherein $R_1$ is $R_3$ and $R_2$ is hydrogen, $R_3$ is —NHCO—$R_4$, and $R_4$ is 1-phenyl-5-(trifluoromethyl)-1H-pyrazolyl; or phenyl substituted with two substituents each independently selected from the group consisting of $C_{1-4}$ haloalkyl, morpholino, imidazolyl substituted with methyl, and piperazinyl substituted with methyl.

6. The compound or a pharmaceutically acceptable salt thereof according to claim 1, wherein $R_4$ is phenyl substituted with two substituents, wherein one substituent is $C_{1-4}$ haloalkyl, and the other substituent is selected from the group consisting of morpholino, imidazolyl substituted with methyl, and piperazinyl substituted with methyl.

7. The compound or a pharmaceutically acceptable salt thereof according to claim 1, wherein $R_4$ is phenyl substituted with two substituents, wherein one substituent is trifluoroalkyl, and the other substituent is selected from the group consisting of morpholino, 2-methyl-1H-imidazol-1-yl, 4-methyl-1H-imidazol-1-yl, 5-methyl-1H-imidazol-1-yl and 4-methylpiperazine-1-yl.

8. The compound or a pharmaceutically acceptable salt thereof according to claim 1 wherein the compound is selected from the group consisting of:

1) 5-methyl-N-(2-methyl-4-(4-morpholino-3-(trifluoromethyl)benzamido)phenyl)isoxazole-4-carboxamide,
2) 5-methyl-N-(2-methyl-4-(3-(4-methylpiperazin-1-yl)-5-(trifluoromethyl)benzamido)phenyl)isoxazole-4-carboxamide,
3) 5-methyl-N-(2-methyl-5-(3-(4-methylpiperazin-1-yl)-5-(trifluoromethyl)benzamido)phenyl)isoxazole-4-carboxamide,
4) 5-methyl-N-(2-methyl-5-(4-morpholino-3-(trifluoromethyl)benzamido)phenyl)isoxazole-4-carboxamide,
5) N-(5-(4-chloro-3-(trifluoromethyl)benzamido)-2-methylphenyl)-5-methylisoxazole-4-carboxamide,
6) N-(5-(3-chlorobenzamido)-2-methylphenyl)-5-methylisoxazole-4-carboxamide,
7) N-(5-(4-chlorobenzamido)-2-methylphenyl)-5-methylisoxazole-4-carboxamide,
8) N-(5-(2-(2-fluorophenyl)acetamido)-2-methylphenyl)-5-methylisoxazole-4-carboxamide,
9) 5-methyl-N-(2-methyl-5-(3-(2-methyl-1H-imidazol-1-yl)-5-(trifluoromethyl)benzamido)phenyl)isoxazole-4-carboxamide,
10) 5-methyl-N-(2-methyl-5-(3-(5-methyl-1H-imidazol-1-yl)-5-(trifluoromethyl)benzamido)phenyl)isoxazole-4-carboxamide,
11) 5-methyl-N-(2-methyl-5-(3-(4-methyl-1H-imidazol-1-yl)-5-(trifluoromethyl)benzamido)phenyl)isoxazole-4-carboxamide,
12) 5-methyl-N-(2-methyl-5-(quinoline-2-carboxamido)phenyl)isoxazole-4-carboxamide,
13) N-(5-(2,2-bis(4-chlorophenyl)acetamido)-2-methylphenyl)-5-methylisoxazole-4-carboxamide,
14) N-(5-(6-hydroxy-2,5,7,8-tetramethylchroman-2-carboxamido)-2-methylphenyl)-5-methylisoxazole-4-carboxamide,
15) N-(5-(1-acetylpiperidine-4-carboxamido)-2-methylphenyl)-5-methylisoxazole-4-carboxamide,
16) N-(5-(2-(1H-indol-3-yl)acetamido)-2-methylphenyl)-5-methylisoxazole-4-carboxamide,
17) 5-methyl-N-(2-methyl-5-(pyrazine-2-carboxamido)phenyl)isoxazole-4-carboxamide,
18) N-(5-(1H-benzo[d][1,2,3]triazole-5-carboxamido)-2-methylphenyl)-5-methylisoxazole-4-carboxamide,
19) N-(5-(indoline-2-carboxamido)-2-methylphenyl)-5-methylisoxazole-4-carboxamide,
20) N-(5-(isonicotinamido)-2-methylphenyl)-5-methylisoxazole-4-carboxamide,
21) N-(5-(2-(2-cyanophenylthio)benzamido)-2-methylphenyl)-5-methylisoxazole-4-carboxamide,
22) N-(5-(2-(biphenyl-4-yl)acetamido)-2-methylphenyl)-5-methylisoxazole-4-carboxamide,
23) 5-methyl-N-(2-methyl-5-(1-phenyl-5-(trifluoromethyl)-1H-pyrazole-4-carboxamido)phenyl)isoxazole-4-carboxamide,
24) N-(5-(3,5-dimethylbenzamido)-2-methylphenyl)-5-methylisoxazole-4-carboxamide,
25) N-(5-biphenyl-2-ylcarboxamido-2-methylphenyl)-5-methylisoxazole-4-carboxamide,
26) N-(5-biphenyl-4-ylcarboxamido-2-methylphenyl)-5-methylisoxazole-4-carboxamide,
27) 5-methyl-N-(2-methyl-5-(quinoline-3-carboxamido)phenyl)isoxazole-4-carboxamide,
28) N-(5-(3-(4-chlorophenyl)ureido)-2-methylphenyl)-5-methylisoxazole-4-carboxamide,
29) 5-methyl-N-(2-methyl-5-(3-(3-(trifluoromethyl)phenyl)ureido)phenyl)isoxazole-4-carboxamide,
30) N-(5-(3-(4-chloro-3-(trifluoromethyl)phenyl)ureido)-2-methylphenyl)-5-methylisoxazole-4-carboxamide,
31) N-(5-(3-(2-fluorophenyl)ureido)-2-methylphenyl)-5-methylisoxazole-4-carboxamide,
32) N-(5-(3-(3-chlorophenyl)ureido)-2-methylphenyl)-5-methylisoxazole-4-carboxamide,
33) N-(5-(3-(3,5-dichlorophenyl)ureido)-2-methylphenyl)-5-methylisoxazole-4-carboxamide,
34) N-(5-(3-(3,4-dichlorophenyl)ureido)-2-methylphenyl)-5-methylisoxazole-4-carboxamide,
35) N-(4-(3-(4-chloro-3-(trifluoromethyl)phenyl)ureido)-2-methylphenyl)-5-methylisoxazole-4-carboxamide,
36) 5-methyl-N-(2-methyl-4-(3-(3-(trifluoromethyl)phenyl)ureido)phenyl)isoxazole-4-carboxamide, 37) N-(4-(3-(3-chlorophenyl)ureido)-2-methylphenyl)-5-methylisoxazole-4-carboxamide,
38) N-(4-(3-(2-fluorophenyl)ureido)-2-methylphenyl)-5-methylisoxazole-4-carboxamide,
39) N-(4-(3-(4-chlorophenyl)ureido)-2-methylphenyl)-5-methylisoxazole-4-carboxamide,
40) N-(4-(3-(3,4-dichlorophenyl)ureido)-2-methylphenyl)-5-methylisoxazole-4-carboxamide,
41) N-(4-(3-(3,5-dichlorophenyl)ureido)-2-methylphenyl)-5-methylisoxazole-4-carboxamide,
42) 5-methyl-N-(2-methyl-5-(propylsulfonamido)phenyl)isoxazole-4-carboxamide,
43) 5-methyl-N-(2-methyl-4-(propylsulfonamido)phenyl)isoxazole-4-carboxamide, and
44) 5-methyl-N-(2-methyl-5-(3-morpholino-5-(trifluoromethyl)benzamido)phenyl)isoxazole-4-carboxamide.

9. A pharmaceutical composition for the treatment of FMS kinase-associated diseases comprising the compound according to claim 1 or a pharmaceutically acceptable salt thereof as an active ingredient.

10. The pharmaceutical composition according to claim 9 wherein the FMS kinase-associated diseases are leukemia, osteoporosis, rheumatoid arthritis or Crohn's disease.

* * * * *